US 9,683,015 B2

(12) United States Patent
Aucagne et al.

(10) Patent No.: US 9,683,015 B2
(45) Date of Patent: Jun. 20, 2017

(54) PEPTIDE C ALPHA-AMIDES, METHODS FOR PREPARING SAME AND USES THEREOF AS PRECURSORS OF PEPTIDE C ALPHA-THIOESTERS FOR PROTEIN SYNTHESIS

(71) Applicant: CENTRE NATIONAL DE LA RECHERCHE SCIENTIFIQUE-CNRS, Paris (FR)

(72) Inventors: Vincent Aucagne, Fleury-les-Aubrais (FR); Agnès Delmas, Orléans (FR); Hélène Adihou, Orléans (FR)

(73) Assignee: CENTRE NATIONAL DE LA RECHERCHE SCIENTIFIQUE-CNRS, Paris (FR)

( * ) Notice: Subject to any disclaimer, the term of this patent is extended or adjusted under 35 U.S.C. 154(b) by 23 days.

(21) Appl. No.: 14/370,416

(22) PCT Filed: Dec. 21, 2012

(86) PCT No.: PCT/FR2012/053074
§ 371 (c)(1),
(2) Date: Jul. 2, 2014

(87) PCT Pub. No.: WO2013/102723
PCT Pub. Date: Jul. 11, 2013

(65) Prior Publication Data
US 2015/0018519 A1    Jan. 15, 2015

(30) Foreign Application Priority Data
Jan. 3, 2012    (FR) ..................... 12 50060

(51) Int. Cl.
| C07C 7/06 | (2006.01) |
| C07K 1/04 | (2006.01) |
| C07K 1/06 | (2006.01) |
| C07K 1/08 | (2006.01) |
| C07K 1/10 | (2006.01) |
| C07K 7/06 | (2006.01) |
| C07K 1/02 | (2006.01) |
| C07K 1/12 | (2006.01) |
| C07K 7/08 | (2006.01) |

(52) U.S. Cl.
CPC ............... C07K 7/06 (2013.01); C07K 1/026 (2013.01); C07K 1/04 (2013.01); C07K 1/042 (2013.01); C07K 1/122 (2013.01); C07K 7/08 (2013.01)

(58) Field of Classification Search
None
See application file for complete search history.

(56) References Cited

U.S. PATENT DOCUMENTS
2011/0184148 A1    7/2011    Hojo et al.

FOREIGN PATENT DOCUMENTS

| WO | WO-2006/013209 A2 | 2/2006 |
| WO | WO-2011/058188 A1 | 5/2011 |
| WO | WO-2013/102723 A1 | 7/2013 |

OTHER PUBLICATIONS

Gross et al., J. Peptide Res. (2005) 65, 395-410.*
Dawson P. et al., Synthesis of proteins by native chemical ligation, Science, 266(5186):776-779 (1994).
Hou, W. et al., Peptidyl N,N-Bis(2-mercaptoethyl)-amides as Thioester Precursors for Native Chemical Ligation, Organic Letters, 13(3):386-389 (2011).
International Searching Authority, International Search Report for PCT/FR2012/053075, issued Apr. 26, 2013.
International Searching Authority, Written Opinion for PCT/FR2012/053075, issued Apr. 26, 2013.
Johnson T. et al., A reversible protecting group for the amide bond in peptides. Use in the synthesis of "difficult sequences", J. Chem. Soc. Chem. Commun., 4:369-374 (1993).
Merrifield, B., Solid phase synthesis, Science, 232(4748):341-347 (1986).
Ollivier N. et al., Bis(2-sulfurnylethyl)amino native peptide ligation, Organic Letters, 12(22):5238-5241 (2010).
Sato, K. et al., N-Sulfanylethylanilide Peptide as a Crypto-Thioester Peptide, ChemBioChem, 12(12):1840-1844 (2011).
Zhang L. et al.; Orthogonal coupling of unprotected peptide segments through histidyl amino terminus, Tetrahedron Letters, 38(1):3-6 (1997).

* cited by examiner

*Primary Examiner* — Marcela M Cordero Garcia
*Assistant Examiner* — Catherine Mader
(74) *Attorney, Agent, or Firm* — Marshall, Gerstein & Borun LLP

(57) ABSTRACT

The subject matter of the present invention is peptide $C^\alpha$-amides which are precursors of peptide $C^\alpha$-thioesters, characterized in that they comprise the radical of general formula (I) in which X, $R_1$, $R_2$, $R_3$, $R_4$, $R_5$, $R_6$, $R_7$, $R_8$, $R_9$, n and A are as defined in Claim 1. The subject matter of the present invention is also the use of these peptide $C^\alpha$-amides for obtaining peptide $C^\alpha$-thioesters. The subject matter of the present invention is also the use of these peptide $C^\alpha$-amides for obtaining peptides or proteins, in particular of therapeutic interest, by direct use as a crypto-thioester partner in NCL reactions.

14 Claims, 20 Drawing Sheets

Details of the steps of Solid Phase Peptide Synthesis (SPPS) illustrated by the synthesis of a peptide of sequence MFCHRLYG (random sequence)

Boc and Fmoc protective groups for the amine function t-Butyloxycarbonyl Boc group Fluorenylmethyloxycarbonyl Fmoc group Native chemical ligation ("NCL")

Use of peptide $C^{\alpha}$-*N*-alkyl-*N*-(β-mercaptoalkyl)-amides (e) or of peptide $C^{\alpha}$-*N*-aryl-*N*-(β-mercaptoalkyl)-amides (e) for:

- the synthesis of peptide $C^{\alpha}$-thioesters (a) (by acyl transfer from N to S) (fig. 4-1 and 4-2),
- direct use in NCL (fig. 4-3).

Fig. 4-1: Details of the N/S acyl transfer

Fig. 4-2: Trans-thioesterification reaction in an acidic medium

Fig. 4-3: Direct use in NCL

Scheme of the principle of the synthesis of peptide $C^\alpha$-β-mercapto-amides of type (e), detailing the difficult step of N-acylation of the secondary amine Comparison between the acylation of a secondary amine bearing a 2-hydroxybenzyl group (j) and that of a secondary amine bearing a 2-methoxybenzyl group (m)

Preparation of six compounds corresponding to general formula (Ia) (namely compounds 3a, 3b, 3c, 3'a, 3'b and 3'c)

Preparation of a peptide C$^\alpha$-amide of general formula (II) (compounds 5 and 5') from a compound of general formula (Ia) (compound 3a)

Chromatogram of an HPLC/MS analysis of the peptide 2'

Chromatogram of an HPLC/MS analysis of the peptide 3'a

Chromatogram of an HPLC/MS analysis of the peptide 3'b

Chromatogram of an HPLC/MS analysis of the peptide 3'c

Chromatogram of an HPLC/MS analysis of the peptide 4'a

Chromatogram of an HPLC/MS analysis of the peptide 4'b

Chromatogram of an HPLC/MS analysis of the peptide 5'

Use of the peptide 5' in a thioesterification reaction in an acidic medium in order to obtain the peptide 6

Use of the peptide 5' in an NCL native chemical ligation reaction in order to obtain a peptide 9

Preparation of three compounds corresponding to general formula (Ia) (namely compounds 12, 13 and 13')

Chromatogram of an HPLC/MS analysis of compound 13'

Preparation of a peptide C^α-amide of general formula (II) (compounds 14 and 14') from a compound of general formula (Ia) (compound 12)

Chromatogram of an HPLC/MS analysis of the peptides 14' and 14''

Preparation of a peptide $C^\alpha$-amide of general formula (II) (compounds 15 and 15') from a compound of general formula (Ia) (compound 13)

Chromatogram of an HPLC/MS analysis of the peptide 15'

Use of the peptides 14'/14'' in an NCL native chemical ligation reaction to give a peptide 17, followed by a one-pot oxidative folding in order to obtain a peptide 19

Chromatogram of an HPLC/MS analysis of the peptide 16

Chromatogram of an HPLC/MS analysis of the purified peptide 17

Chromatogram of an HPLC/MS analysis of the purified peptide 19

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Group B

<400> SEQUENCE: 1

Leu Tyr Arg Ala Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Peptidyl resin

<400> SEQUENCE: 2

Cys Leu Tyr Arg Ala Gly
```

```
<210> SEQ ID NO 3
<211> LENGTH: 4
<212> TYPE: PRT
<213> ORGANISM: Artificial Sequence
<220> FEATURE:
<223> OTHER INFORMATION: Peptide 1

<400> SEQUENCE: 3

Tyr Arg Phe Gly
1

<210> SEQ ID NO 4
<211> LENGTH: 10
<212> TYPE: PRT
<213> ORGANISM: Artificial Sequence
<220> FEATURE:
<223> OTHER INFORMATION: Peptide 9

<400> SEQUENCE: 4

Tyr Arg Phe Gly Cys Leu Tyr Arg Ala Gly
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Peptide 1

<400> SEQUENCE: 5

Ala Ser Cys Asn Gly Val Cys Pro Phe Glu Met Pro Pro Cys Gly Thr
1               5                   10                  15

Ser Ala

<210> SEQ ID NO 6
<211> LENGTH: 17
<212> TYPE: PRT
<213> ORGANISM: Artificial Sequence
<220> FEATURE:
<223> OTHER INFORMATION: Peptide 16

<400> SEQUENCE: 6

Cys Arg Cys Ile Pro Val Gly Leu Ile Gly Tyr Cys Arg Asn Pro Ser
1               5                   10                  15

Gly
```

PEPTIDE C ALPHA-AMIDES, METHODS FOR PREPARING SAME AND USES THEREOF AS PRECURSORS OF PEPTIDE C ALPHA-THIOESTERS FOR PROTEIN SYNTHESIS

CROSS REFERENCE TO RELATED APPLICATIONS

The present application is filed pursuant to 35U.S.C. §371as the U.S. National Phase of International Patent Application No. PCT/FR2012/053074, filed Dec. 21, 2012, claiming the benefit of priority to French Patent Application No. FR 12 50060, filed Jan. 3, 2012. The content of each of the aforementioned patent applications is incorporated herein by reference in its entirety.

The present invention relates to novel peptide $C^\alpha$-amides, the advantage of which lies in the fact that they are direct precursors of peptide $C^\alpha$-thioesters, to the methods for preparing said peptides and to the uses thereof for protein synthesis, in particular the synthesis of proteins of therapeutic interest.

Proteins are biological macromolecules which are ubiquitous in the living world and some of which have a strong therapeutic potential. They are linear oligomers of α-amino acids (denoted H—Xaa-OH) linked via amide bonds. Small proteins (less than about fifty Xaa residues) are called peptides. In order to be able to study their possible therapeutic applications, it is essential to be able to readily produce them in sufficient amount. The proteins required for these studies can be obtained via two routes. The biotechnological method, which involves the "recombinant DNA" technique, is often used but has many limitations. Chemical synthesis is a very advantageous additional technique for the production of proteins comprising up to more than two hundred α-amino acid residues. It makes it possible to obtain proteins that are difficult to obtain via biotechnology, such as cytotoxic proteins or proteins which are specifically modified, both on the side chains of the residues introduced (post-translational modifications, probes, polyethylene glycol chains, etc.), but also on the peptide backbone and the N- and C-terminal ends.

The chemical synthesis of small proteins can be carried out by Solid Phase Peptide Synthesis (SPPS) (Merrifield, B. Solid phase synthesis, *Science* 1986, 232, 341-347). SPPS is a technique which makes it possible, by means of an "arm", to attach a C-terminal amino acid which has suitable protective groups on a solid support, generally an insoluble polymer called "resin". The subsequent amino acids are added one by one until the N-terminus is reached, by means of a succession of chemical coupling and deprotection reactions. In this way, it is possible to use very large excesses of reagents, thereby considerably increasing the reaction yields. The only purification which then becomes necessary is abundant rinsing of the resin, carried out by simple filtration after each reaction, the intermediate chromatographic purification steps being eliminated. The arm is inert under all the conditions of the synthesis and allows release of the peptide in solution only during a final arm cleavage step, usually concomitant with the deprotection of the side chains. The details of the Solid Phase Peptide Synthesis (SPPS) steps are illustrated in FIG. 1.

Two principal synthesis strategies have been developed in SPPS, namely Boc strategy SPPS and Fmoc stragegy SPPS, which involve, respectively, α-amino acids $N^\alpha$-protected either with a t-butyloxycarbonyl (Boc) group or with a fluorenylmethyloxycarbonyl (Fmoc) group. These two Boc and Fmoc protective groups are illustrated in FIG. 2. Boc-strategy SPPS requires a final treatment with hydrogen fluoride (HF) which is dangerous and difficult to carry out, and is consequently increasingly neglected. Fmoc-strategy SPPS (Fmoc SPPS) is more widely used these days.

SPPS is limited in terms of size of the proteins that can be routinely synthesized (<~50 amino acid residues). An alternative method consists in synthesizing protein fragments via SPPS which can be condensed by virtue of highly chemoselective reactions. These reactions are generally carried out in a buffered aqueous medium between deprotected peptide partners and are called chemical ligations. When the bond which results from the ligation is an amide bond, the chemical ligation is termed "native" (Dawson P. et al.; Synthesis of proteins by native chemical ligation, *Science* 1994, 266, 776-779). The "Native Chemical Ligation: NCL" technique most widely used is illustrated in FIG. 3. This reaction is today the reference method for the chemical synthesis of proteins. This technique involves a peptide of which the C-terminus is modified with a $C^\alpha$-thioester (see compound called (a) in FIG. 3 with R' representing a radical originating from a thiol of formula R'—SH) and a peptide bearing an N-terminal cysteine (see compound called (b)). Firstly, the sulfhydryl group of the N-terminal cysteine of the compound (b) reacts, via a trans-thioesterification reaction, with the thioester function of (a). The compound (c) which results therefrom rearranges spontaneously by acyl transfer from the sulfur to the nitrogen (S→N) via a five-membered cyclic transition state, which is highly thermodynamically favored. A peptide (d) which has an amide bond at the junction between the two fragments is thus obtained.

Contrary to the synthesis of peptide $C^\alpha$-acids and $C^\alpha$-amides, peptide $C^\alpha$-thioesters are particularly difficult to synthesize by Fmoc SPPS owing to the non-compatibility of the thioester function (—CO—S—) with the piperidine used to deprotect the Fmoc group. Piperidine is in fact a nucleophilic amine which rapidly reacts with thioester functions to cleave the carbon-sulfur bond and to give the corresponding amide and thiol. The vast majority of the contemporary strategies for the synthesis of peptide thioesters by Fmoc SPPS are indirect methods: the thioester function is introduced only after having carried out the complete extension of the peptide.

Among the various existing methods for synthesizing peptide $C^\alpha$-thioesters by Fmoc SPPS (FIG. 4-2, compound (a)), some involve peptide $C^\alpha$-N-alkyl-N-(β-mercaptoalkyl)-amides (FIG. 4-1, compound (e) with R=alkyl and R" representing a group comprising a function having made it possible, during the first steps of the synthesis of (e), to graft a precursor of (e) to an insoluble polymer by means of an arm) or peptide $C^\alpha$-N-aryl-N-(β-mercaptoalkyl)-amides (FIG. 4-1, compound (e) with R=aryl and R" as previously defined).

Such peptide $C^\alpha$-β-mercapto-amides (e) are generally spontaneously in equilibrium with a $C^\alpha$-β-amino-thioester form (f) via an intramolecular acyl transfer from the nitrogen to the sulfur (N→S) detailed in FIG. 4-1. The equilibrium is shifted toward the amide form (e) under neutral or basic conditions, whereas the thioester form (f) predominates in an acidic medium. Reaction with an excess of thiol (R'SH), at an acidic pH, of compounds of (e) or (f) type makes it possible to gradually shift this equilibrium and to obtain the peptide $C^\alpha$-thioester (a) devoid of β-amine function (compound (a)).

It has been shown in several recent examples that some of these peptide $C^\alpha$-β-mercapto-amides (e) can be used directly, in the same way as the peptide $C^\alpha$-thioesters (f), under NCL conditions, i.e. in the presence of a peptide which has an N-terminal cysteine of type (b) and of an excess of thiol R'SH, in a medium buffered at a pH close to neutrality. The principle is, a priori, that the N→S acyl transfer and the trans-thioesterification take place in situ at the time of the ligation (FIG. 4-3). The peptide $C^\alpha$-β-mercapto-amides (e) which have this property are called "crypto-thioesters". Only a few examples have been described to date (1-Ollivier N. et al.; Bis(2-sulfurnylethyl) amino native peptide ligation, Org. Lett. 2010, 12, 5238-5241; 2-Sato K. et al.; Nsulfurnylethylanilide peptide as a crypto-thioester peptide, ChemBioChem 2011, 12, 1840-1844; 3-Hou W. et al.; Peptidyl N,N-bis(2-mercaptoethyl)-amides as thioester precursors for native chemical ligation. Organic Letters 2011, 13, 386-389).

The synthesis of peptide $C^\alpha$-N-alkyl-N-(β-mercaptoalkyl)-amides or $C^\alpha$-N-aryl-N-(β-mercaptoalkyl)-amides (see FIG. 5-1, compound (e) with R=alkyl or aryl) is carried out by Fmoc SPPS while masking the thiol function of the compound (h) with a protective group (Protec), the consequence of which is to prevent rearrangement in a thioester form of type (f) (FIG. 4-3). The peptide remains in its amide form, and is therefore stable throughout the elongation.

The main drawback of this approach of the synthesis of thioesters or of crypto-thioesters lies in the fact that all the syntheses described to date have in common an extremely difficult first step of N-acylation (FIG. 5-1). Indeed, because of the steric hindrance around the nitrogen atom, the reaction kinetics are generally very slow, which can result in incomplete N-acylation, unwanted by-products and low yields. In many cases, this approach is limited in practice to peptide $C^\alpha$-thioesters which have a glycine residue in the C-terminal position.

There still remains therefore the need to synthesize peptide $C^\alpha$-N-alkyl-N-(β-mercaptoalkyl)-amides or $C^\alpha$-N-aryl-N-(β-mercaptoalkyl)-amides by means of a simple and efficient method. Indeed, a simple and efficient preparation of such peptide $C^\alpha$-amides allows in particular a simple and efficient preparation of peptide $C^\alpha$-thioesters, since these peptide $C^\alpha$-amides are direct precursors of peptide $C^\alpha$-thioesters.

In addition, such peptide $C^\alpha$-amides may also have crypto-thioester properties, and may be used directly in an NCL reaction without it being necessary to isolate the thioester form beforehand.

Advantageously according to the invention, the N-acylation of the secondary amine of type (h) (FIG. 5-1) is advantageously accelerated, in particular by virtue of an entirely original radical R which allows intramolecular assistance during the N-acylation.

The principle of such an assistance for the acylation of a secondary amine has been described in the literature, but never applied to peptide $C^\alpha$-β-mercapto-amide precursors of $C^\alpha$-thioesters. By way of example, mention may be made of the assistance of the acylation of a secondary amine of a peptide by an N-(2-hydroxybenzyl) function (Johnson T. et al.; A reversible protecting group for the amide bond in peptides. Use in the synthesis of "difficult sequences", J. Chem. Soc. Chem. Commun., 1993, 369-374).

This assistance is illustrated in FIG. 5-2. The N-acylation of the secondary amine (j) is much faster than that of the secondary amine (m), even though the steric hindrance around the nitrogen atom (principal factor determining the kinetics of a conventional N-acylation reaction) of each of these two compounds is comparable. This great difference in reactivity is due to the presence of an N-(2-hydroxybenzyl) group in (j) but not in (m). The hydroxyl function of this group can be O-acylated under N-acylation conditions, to give an intermediate (k). Contrary to the secondary amine function, the hydroxyl function is barely hindered at all, and this O-acylation reaction is rapid. The intermediate (k) will rapidly undergo acyl transfer from the oxygen to the nitrogen (O→N) so as to give the amide (l) via a six-membered cyclic transition state which is highly thermodynamically favored. This N-acylation by intramolecular acyl transfer resulting in (l) is hardly at all sensitive to the steric hindrance around the nitrogen atom, contrary to the intermolecular version resulting in (n), thereby explaining the much faster N-acylation of (j) compared with (m). A similar assistance has also been mentioned during the acylation of peptides which have an amine function that has a group of γ-(2-azaheterocycle) type (Zhang L. et al.; Orthogonal coupling of unprotected peptide segments through histidyl amino terminus, Tetrahedron Lett. 1997, 38, 3-6).

One of the objectives of the present invention is to provide a method for the synthesis of peptide $C^\alpha$-N-alkyl-N-(β-mercaptoalkyl)-amide precursors of peptide $C^\alpha$-thioesters which is at the same time simple to carry out, rapid and inexpensive, and which does not generate unwanted by-products.

Advantageously according to the invention, some of the groups present on the original radicals R as mentioned previously may also allow intramolecular assistance of the N→S acyl transfer and/or of the trans-thioesterification, and thus increase the ability of the peptide $C^\alpha$-N-alkyl-N-(β-mercaptoalkyl)-amides of the invention to behave like crypto-thioesters. This assistance may result, for example, from the formation of hydrogen bonds, dipole interactions, π-π interactions, or acid-base catalysis.

Another objective of the invention is to provide a method for the synthesis of original peptide $C^\alpha$-N-alkyl-N-(β-mercaptoalkyl)-amides which have crypto-thioester properties in order to be able to be directly used as a partner in NCL reactions.

In the present application, the peptide $C^\alpha$-N-alkyl-N-(β-mercaptoalkyl)-amides will be more simply referred to as peptide $C^\alpha$-amides. The peptide $C^\alpha$-amides of the invention cover both said peptide $C^\alpha$-N-alkyl-N-(β-mercaptoalkyl)-amides and also peptide $C^\alpha$-N-alkyl-N-(γ-mercaptoalkyl)-amides, $C^\alpha$-N-alkyl-N-(β-selenoalkyl)-amides and $C^\alpha$-N-alkyl-N-(γ-selenoalkyl)-amides, said peptide $C^\alpha$-amides of the invention being precursors of peptide $C^\alpha$-thioesters, according to a presumed mechanism of acyl transfer from the sulfur or the selenium to the nitrogen.

The peptide $C^\alpha$-amides of the invention may also be referred to as "crypto-thioester" peptides owing to the possibility of using them directly in NCL reactions, without it being necessary to prepare the thioester form beforehand.

A subject of the present invention is thus a peptide $C^\alpha$-amide precursor of a peptide $C^\alpha$-thioester, characterized in that it comprises the radical of general formula (I):

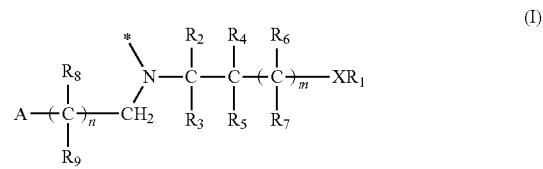

in which

X represents a sulfur or selenium atom, $R_1$ represents a hydrogen atom or a protective group for the sulfur or for the selenium which is compatible with conditions of elongation by Fmoc SPPS, m represents an integer equal to 0 or 1, one of $R_2$, $R_3$, $R_4$, $R_5$, $R_6$ or $R_7$ represents the radical —B—C-D in which:

D represents a hydrogen atom or a solid support suitable for solid phase peptide synthesis (SPPS), C is absent or represents an arm that can be used for SPPS, B represents a divalent radical comprising a heteroatom, the others of said $R_2$, $R_3$, $R_4$, $R_5$, $R_6$ or $R_7$ which do not represent —B—C-D, then represent, independently of one another, a hydrogen atom, or an alkyl radical having from 1 to 10 carbon atoms, and preferably a methyl radical (—$CH_3$) or a phenyl radical (—$C_6H_5$), on the condition that at most two of said radicals $R_2$, $R_3$, $R_4$, $R_5$, $R_6$ or $R_7$ represent at the same time a phenyl, $R_8$ and $R_9$ represent, independently of one another, an alkyl radical having from 1 to 10 carbon atoms, and preferably a methyl radical, or a hydrogen atom, n represents an integer ranging from 0 to 4, preferably from 0 to 1, A representing an aryl or heteroaryl radical chosen from the group comprising the radical of formula:

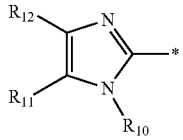

in which $R_{10}$ represents an alkyl radical having from 1 to 10 carbon atoms, and preferably a methyl, $R_{11}$ and $R_{12}$ represent, independently of one another, a hydrogen atom, a halogen atom chosen from the group comprising Cl, Br, I and F, a CN radical, an —$NO_2$ radical, a —$CF_3$ radical, a phenyl radical (—$C_6H_5$), a —$CONH_2$ radical, an $R_{10}$ radical, an —$OR_{10}$) radical, an —$SR_{10}$ radical, an —$N(R_{10})_2$ radical, a —$COOR_{10}$ radical, a —$CONHR_{10}$ radical or a —$CON(R_{10})_2$ radical, $R_{10}$ being as previously defined, the radical of formula:

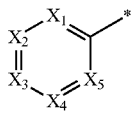

in which at least one of $X_1$, $X_2$, $X_3$, $X_4$ and $X_5$ represents a nitrogen (N) atom, a C—OH radical or a C—SH radical, the others of said $X_1$, $X_2$, $X_3$, $X_4$ or $X_5$ which do not represent N, C—OH or C—SH, then representing, independently of one another, a C—$R_{11}$ radical with $R_{11}$ as previously defined, the radical of formula:

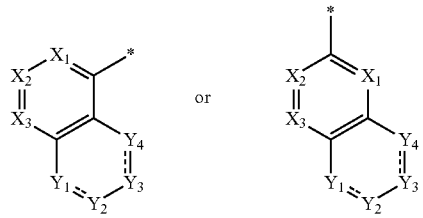

in which at least one of $X_1$, $X_2$, $X_3$ and $Y_4$ represents a nitrogen (N) atom, a C—OH radical or a C—SH radical, the others of said $X_1$, $X_2$ or $X_3$ which do not represent N, C—OH or C—SH, then representing, independently of one another, a C—$R_{11}$ radical with $R_{11}$ as previously defined, $Y_1$, $Y_2$, $Y_3$ and $Y_4$ (on condition that $Y_4$ does not represent C—OH or C—SH) represent, independently of one another, depending on whether they are linked via a single or double bond, a nitrogen (N) atom or an $NR_{10}$ group with $R_{10}$ as previously defined, a CH or $CH_2$ group, a C—$R_{11}$ or $CHR_{11}$ or $CR_{11}R_{12}$ group with $R_{11}$ and $R_{12}$ as previously defined, a carbonyl (C=O), an oxygen (O) atom or a sulfur (S) atom, with the condition that at most two of said $Y_1$, $Y_2$, $Y_3$ and $Y_4$ represent at the same time an oxygen atom or a sulfur atom, one of said $Y_1$, $Y_2$, $Y_3$ or $Y_4$ possibly being absent, so as to form a 5-membered ring.

The term "alkyl" is intended to mean a hydrocarbyl radical having 1 to 10 carbon atoms, corresponding to the general formula $C_nH_{2n+1}$ where n is greater than or equal to 1. The alkyl groups may be linear or branched and may be substituted with the groups indicated in the present application.

The term "aryl" is intended to mean an aromatic polyunsaturated hydrocarbyl group having a single ring (for instance phenyl) or several fused rings (for instance naphthyl) or several rings connected via a covalent bond (for instance biphenyl), which typically contain 5 to 12 carbon atoms, preferentially 6 or 12, and where at least one ring is aromatic. The aromatic ring may optionally comprise one to two additional fused rings (i.e. cycloalkyl, heterocycloalkyl or heteroaryl). The term "aryl" also comprises the partially hydrogenated derivatives of carbocyclic systems described above. The aromatic ring may optionally comprise one to five substituents (other than H) of alkyl (preferentially methyl), —F, —Cl, —Br, —I, —$CF_3$, —OMe, —SMe, —$N(Me)_2$, —COOH, —$SO_3H$, —$CH_2N(Me)_2$, —$CH_2COOH$, —$CH_2SO_3H$, —$CH_2CH_2N(Me)_2$, —$CH_2CH_2COOH$, —$CH_2CH_2SO_3H$, —$OCH_2COOH$, —$OCH_2SO_3H$, —$OCH_2CH_2N(Me)_2$, —$OCH_2CH_2COOH$ or —$OCH_2CH_2SO_3H$ type.

The term "heteroaryl" is intended to mean a ring or several fused rings or rings connected via a covalent bond, comprising 3 to 17 carbon atoms, preferentially 3 to 11 carbon atoms, where at least one of the rings is aromatic and where at least one or more carbon atoms are replaced with oxygen, nitrogen and/or sulfur. The term "heteroaryl" also comprises systems described above having a fused aryl, cycloalkyl, heteroaryl or heterocycloalkyl group or one to five alkyl, preferentially methyl, substituents. The term "heteroaryl" also comprises systems described above comprising one to four substituents (other than H) of alkyl (preferentially methyl), —F, —Cl, —Br, —I, —$CF_3$, —OMe, —SMe, —$N(Me)_2$, —COOH, —$SO_3H$, —$CH_2N$ (Me)$_2$, —CH$_2$COOH, —CH$_2$SO$_3$H, —CH$_2$CH$_2$N(Me)$_2$, —CH$_2$CH$_2$COOH, —CH$_2$CH$_2$SO$_3$H, —OCH$_2$COOH, —OCH$_2$SO$_3$H, —OCH$_2$CH$_2$N(Me)$_2$, —OCH$_2$CH$_2$COOH or —OCH$_2$CH$_2$SO$_3$H type.

The term "cycloalkyl" is intended to mean a saturated or unsaturated, cyclic monovalent hydrocarbyl having one or two rings and comprising 3 to 10 carbon atoms.

The term "heterocycloalkyl" is intended to mean a cycloalkyl in which at least one carbon atom is replaced with an oxygen, nitrogen and/or sulfur atom.

According to one advantageous embodiment of the invention, the divalent radical B present in the radical (I), represents:

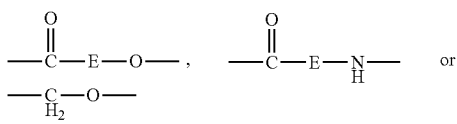

in which
E is absent or represents the -(Xaa)$_i$- group in which:
i represents an integer ranging from 1 to 20, and preferably from 1 to 5,
each Xaa represents, independently of one another, an amino acid residue, and
when i is greater than or equal to 2, each of said Xaa is connected to its neighboring Xaa via a peptide bond,
or, in the case where m=1, and R$_4$ or R$_5$=—B—C-D, then the divalent radical B preferably represents:

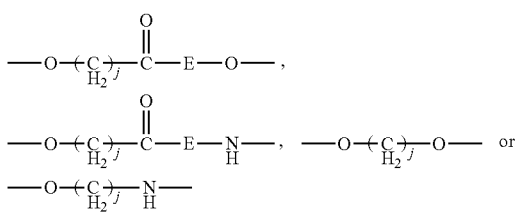

in which:
j represents an integer ranging from 0 to 10, preferably from 0 to 3, and E is as previously defined.

The possible reactive functions of the side chains of said amino acid residues may be free, i.e. unprotected, or conversely protected with protective groups normally used by those skilled in the art during SPPS.

According to another advantageous embodiment of the invention, in the radical (I), C represents an arm that can be used for Fmoc SPPS, and preferably an acid-labile arm chosen from the group comprising a Rink (4-[(2,4-dimethoxyphenyl)methyl]phenoxyacetyl) arm, a Wang (4-alkoxybenzyl) arm, a Sieber (xanthen-3-yloxyalkyl) arm, a PAL (4-2,5-dimethoxyalkoxybenzyl) arm, a 2-chlorotrityl arm, a PAM (phenylacetamidomethyl) arm, a SASRIN (2-methoxy-4-alkoxybenzyl) arm or an MBHA (4-methyl) benzhydryl arm.

According to another advantageous embodiment of the invention, in the radical (I), D represents a solid support suitable for Fmoc SPPS and is preferably chosen from the group comprising a resin sold under the name Pega®, a resin sold under the name Chemmatrix™, a polyacrylamide resin, a polystyrene resin or a polystyrenepolyethylene glycol (PEG) mixed resin.

By way of example of a polystyrenepolyethylene glycol (PEG) mixed resin, mention may be made of those sold under the name tentagel or argogel.

According to one advantageous embodiment of the invention, in the radical (I), n is an integer equal to 0, and the radical A has the formula:

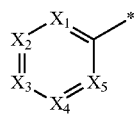

in which X$_1$ represents C—OH, and each of X$_2$, X$_3$, X$_4$ and X$_5$ is as previously defined.

Preferably, each of X$_2$, X$_3$ or X$_5$ represents CH and X$_4$ represents C—R$_{11}$ with R$_{11}$ as previously defined.

Even more preferably, X$_4$ represents CH, C-OMe or C—NO$_2$.

Thus, a preferred radical A is the one represented by one of the following formulae:

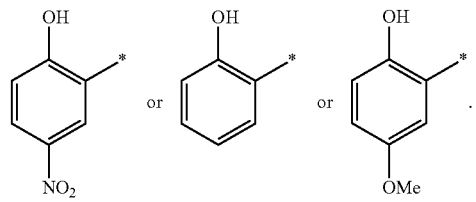 [SMILES: *c1cc([N+](=O)[O-])ccc1O ; *c1ccccc1O ; *c1cc(OC)ccc1O]

According to another advantageous embodiment of the invention, in the radical (I), n is an integer equal to 0, and the radical A has the formula:

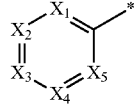

in which X$_1$ represents a nitrogen (N) atom and each of said X$_2$, X$_3$, X$_4$ and X$_5$ is as previously defined. Preferably, each of X$_2$, X$_3$ or X$_5$ represents CH and X$_4$ represents CH or C—R$_{11}$ with R$_{11}$ representing OCH$_3$ or N(CH$_3$)$_2$.

Thus, another preferred radical A is the one represented by one of the following formulae:

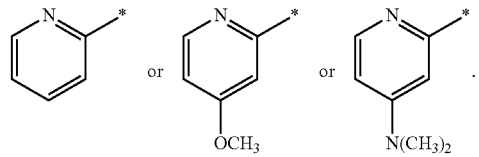 [SMILES: *c1ccccn1 ; *c1cc(OC)ccn1 ; *c1cc(N(C)C)ccn1]

According to another advantageous embodiment of the invention, in the radical (I), n is an integer equal to 1, and the radical A has the formula:

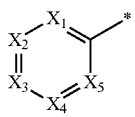

in which $X_1$ represents a nitrogen (N) atom and each of said $X_2$, $X_3$, $X_4$ and $X_5$ is as previously defined. Preferably, each of $X_2$, $X_3$, $X_4$ and $X_5$ represents CH.

Thus, another preferred radical A with n equal to 1 is the one represented by the following formula:

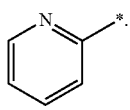

According to another advantageous embodiment of the invention, in the radical (I), n is an integer equal to 0, and the radical A has the formula:

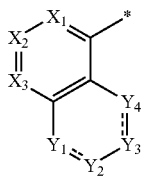

in which $X_1$ or $Y_4$ represents C—OH or N, the other of said $X_1$ or $Y_4$ which does not represent C—OH or N and also each of said $X_2$, $X_3$, $Y_1$, $Y_2$ and $Y_3$ are as previously defined.

According to another advantageous embodiment of the invention, in the radical (I), n is an integer equal to 0, and the radical A has the formula:

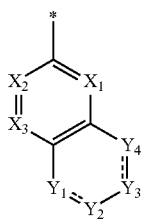

in which $X_1$ or $X_2$ represents C—OH or N, the other of said $X_1$ or $X_2$ which does not represent C—OH or N and also each of said $X_3$, $Y_1$, $Y_2$, $Y_3$ and $Y_4$ are as previously defined.

According to one preferred embodiment of the invention, the peptide $C^\alpha$-amide is characterized in that, in the radical (I):

m represents 0 or 1,
each of said $R_3$, $R_4$, $R_5$, $R_6$ or $R_7$ represents H,
$R_2$ represents —B—C—D in which B represents:

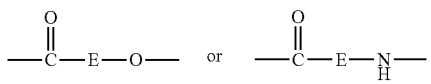

and C, D and E are as previously defined.

According to one preferred embodiment of the invention, in the radical (I), m is equal to 0 and X represents a sulfur (S) atom.

When $R_1$ is a protective group for sulfur, then said group can be chosen from the group comprising trityl (Trt), methyltrityl (Mtt), methoxytrityl (Mmt), xanthenyl (Xan), trimethoxybenzyl (Tmob), acetamidomethyl (Acm), trimethylacetamidomethyl (Tacm), benzamidomethyl (Bam), allyloxycarbonylaminomethyl (Allocam), phthalimidomethyl (Pim), 2-(trimethylsilyl)ethyl, t-butyl (tBu), 2,4,6-trimethylbenzyl, quinolinylmethyl (Qm), diphenyl-4-pyridylmethyl, 1-adamantyl, benzyloxymethyl (BOM), 2-tetrahydropyranyl (Thp), benzylthiomethyl, ethylsulfenyl (SEt), t-butylsulfenyl (StBu), phenylsulfenyl (SPh) and 2,4-dinitrophenyl.

More particularly, according to one advantageous embodiment of the invention, when $R_1$ is a protective group for sulfur which can be cleaved by treatment with trifluoroacetic acid (TFA), then said group is preferably chosen from the group comprising trityl (Trt), methyltrityl (Mtt), methoxytrityl (Mmt), xanthenyl (Xan) and tri-methoxybenzyl (Tmob).

According to another advantageous embodiment of the invention, when $R_1$ is a protective group for sulfur which is stable with respect to treatment with TFA and stable under NCL conditions, then said group is preferably chosen from the group comprising acetamidomethyl (Acm), trimethylacetamidomethyl (Tacm), benzamidomethyl (Bam), allyloxycarbonylaminomethyl (Allocam), phthalimidomethyl (Pim), 2-(trimethylsilyl)ethyl, t-butyl (tBu), 2,4,6-trimethylbenzyl, quinolinylmethyl (Qm), diphenyl-4-pyridylmethyl, 1-adamantyl, benzyloxymethyl (BOM), 2-tetrahydropyranyl (Thp) and benzylthiomethyl.

According to yet another advantageous embodiment of the invention, when $R_1$ is a protective group for sulfur which is stable with respect to treatment with TFA, but labile under NCL conditions, then said group is preferably chosen from the group comprising ethylsulfenyl (SEt), t-butylsulfenyl (StBu), phenylsulfenyl (SPh) and 2,4-dinitrophenyl.

According to yet another advantageous embodiment, $R_1$ is a group which is labile in an NCL native chemical ligation reaction and is preferably chosen from the group containing ethylsulfenyl (SEt), t-butylsulfenyl (StBu) and phenylsulfenyl (SPh) groups.

According to one advantageous embodiment of the invention, X represents a selenium (Se) atom, and $R_1$ is a protective group for selenium and is preferably chosen from the group comprising 4-methoxybenzyl (Mob), 4-methylbenzyl (MeBzl) or benzyl (Bzl).

By way of example of a radical (I) according to the invention, mention may be made of one of those chosen from the group comprising:

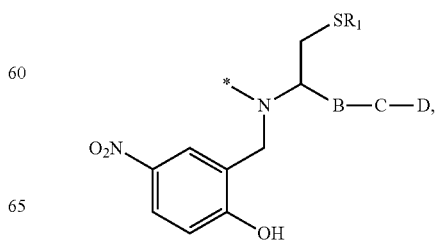

-continued

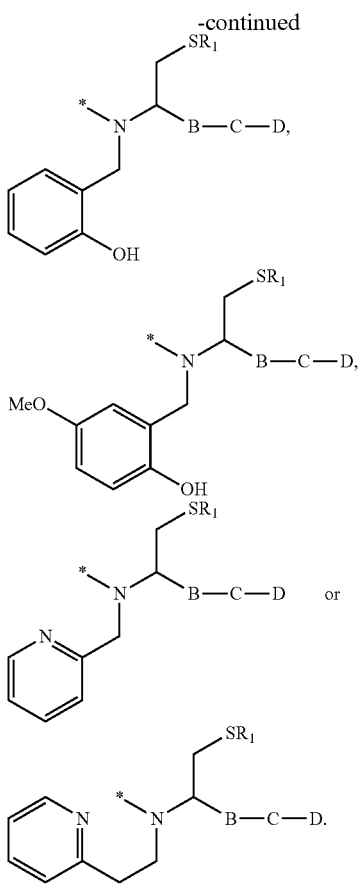

in which:

B represents

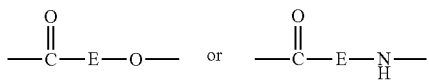

and E, C, D and $R_1$ are as previously defined.

The peptide $C^\alpha$-amide which is the subject of the invention is more particularly characterized in that it has general formula (II):

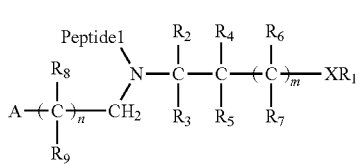

in which:

Peptide1 represents the $R_{18}$-$(Xaa)_k$- group in which:

k is an integer ranging from 1 to 100, preferably from 4 to 60, and even more preferentially from 8 to 40, Xaa represents, independently of one another, an amino acid residue originating from an amino acid of formula H—Xaa-OH, and when k is greater than or equal to 2, each of said Xaa is connected to its neighboring Xaa via a peptide bond, $R_{18}$ is a hydrogen atom or a substituent of the N-terminal end included in the Xaa residue, X, m, n, A and $R_1$ to $R_9$ being as previously defined.

Preferably, in the divalent radical B as defined above, E is absent or represents $-(Xaa)_i-$ which is chosen so as to increase the aqueous solubility of the Peptide 1.

The possible reactive functions of the side chains of the amino acid residues $-(Xaa)_k$ may be free, i.e. unprotected, or conversely protected with protective groups normally used by those skilled in the art during SPPS.

According to a first advantageous embodiment of the invention, the process for preparing the compound of formula (Ia) (said compound (Ia) forming the radical (I) within the peptide $C^\alpha$-amide of the invention) is characterized in that it comprises:

a step of grafting, onto a solid support of formula:

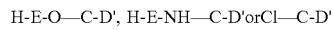

in which E and C are as previously defined, D' represents a resin suitable for SPPS and H, O, NH and Cl correspond to the chemical symbols normally used, a compound of general formula (III):

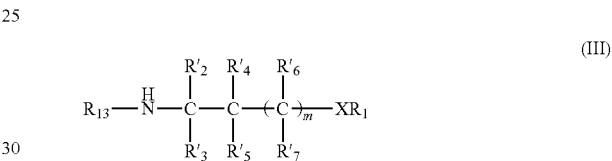

in which:

$R_{13}$ represents a protective group for the amine function, and preferably an Fmoc group, m, X and $R_1$ are as previously defined, one of $R'_2$, $R'_3$, $R'_4$, $R'_5$, $R'_6$ or $R'_7$ representing a reactive group comprising a reactive chemical function preferably chosen from the group comprising —COOH, —NH$_2$ and —OH, and making it possible to graft said compound (III) onto the solid support as mentioned above according to a method known to those skilled in the art for Fmoc SPPS, the others of said $R'_2$, $R'_3$, $R'_4$, $R'_5$, $R'_6$ or $R'_7$ which do not represent said reactive group have the same meaning as said $R_2$, $R_3$, $R_4$, $R_5$, $R_6$ or $R_7$ as previously defined and do not represent —B—C-D, in order to obtain a compound of general formula (IV):

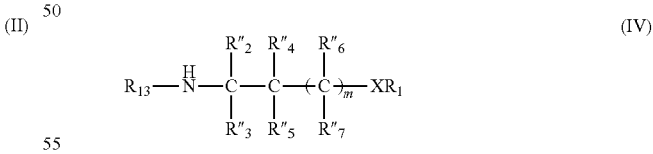

in which:

m, X, $R_1$ and $R_{13}$ are as previously defined, one of $R''_2$, $R''_3$, $R''_4$, $R''_5$, $R''_6$ or $R''_7$ represents —B—C-D' in which B, C and D' are as previously defined, the others of said $R''_2$, $R''_3$, $R''_4$, $R''_5$, $R''_6$ or $R''_7$ which do not represent the radical —B—C-D' have the same meaning as said $R_2$, $R_3$, $R_4$, $R_5$, $R_6$ or $R_7$ as previously defined and do not represent the radical —B—C-D, said grafting step being followed by a step of cleaving the protective group $R_{13}$ of the compound (IV) in order to obtain a compound of general formula (IVa):

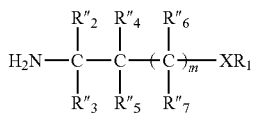
(IVa)

in which:
m, X, $R_1$, $R''_2$, $R''_3$, $R''_4$, $R''_5$, $R''_6$ and $R''_7$ are as previously defined,
said cleaving step being followed by a step of mono-N-alkylation of the compound (IVa) in order to obtain the compound of general formula (V):

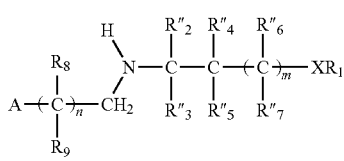
(V)

in which X, $R_1$, m, $R''_2$, $R''_3$, $R''_4$, $R''_5$, $R''_6$, $R''_7$, n, $R_8$, $R_9$ and A are as previously defined,
the compound (V) being a direct precursor of the compound of general formula (Ia):

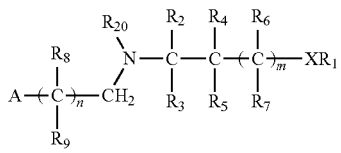
(Ia)

in which:
$R_{20}$=H or $R_{13}$ as previously defined,
X, $R_1$, m, $R_2$, $R_3$, $R_4$, $R_5$, $R_6$, $R_7$, n, $R_8$, $R_9$ and A are as previously defined,
the compound (Ia) being obtained from the compound (V) according to one of the methods known to those skilled in the art.

The compound (Ia) forms the radical (I) within the peptide $C^\alpha$-amide of the invention (see, for example, the compound of general formula (II)).

According to one advantageous embodiment of the process for preparing the compound (Ia) of the invention, the step of mono-N-alkylation of the compound (IVa) comprises a reaction for reductive amination of said compound (IVa) using an aldehyde of general formula (VI):

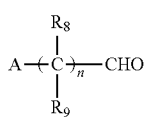
(VI)

in which A, n, $R_8$ and $R_9$ are as previously defined,
in order to form an imine which is reduced so as to form the compound (V) as defined above.

The reduction may, for example, be carried out using a borohydride chosen from the group comprising sodium cyanoborohydride ($NaBH_3CN$), sodium triacetoxyborohydride ($NaBH(OAc)_3$) or sodium borohydride ($NaBH_4$).

According to another advantageous embodiment of the process for preparing the compound (Ia) of the invention, the step of mono-N-alkylation of the compound (IVa) comprises:
a prior step of sulfonylation of the primary amine function of the compound (IVa), in order to obtain the compound of formula (Nb):

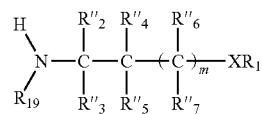
(IVb)

in which $R_{19}$ represents an arylsulfonyl group chosen from the group comprising 2-nitrobenzenesulfonyl, 4-nitrobenzenesulfonyl and 2,4-dinitrobenzenesulfonyl,
m, X, $R_1$, $R''_2$, $R''_3$, $R''_4$, $R''_5$, $R''_6$ and $R''_7$ are as previously defined,
said sulfonylation step being followed by a step of monoalkylation by nucleophilic N-substitution between the compound (Wb) and a compound of general formula (VII):

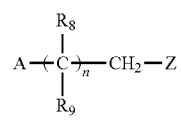
(VII)

in which Z represents a leaving group chosen from the group comprising Cl, Br, I or a sulfonate, it being possible for said sulfonate to be, for example, an "O-mesylate" (—OMs) represented by $MeSO_2$—O—, an "O-tosylate" (—OTs) represented by p-Me-$C_6H_4$—$SO_2$—O— or an "O-triflate" (—OTf) represented by $CF_3SO_2$—O—,
A, n, $R_8$ and $R_9$ are as previously defined,
so as to obtain the compound of formula (Va):

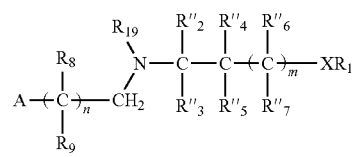
(Va)

in which m, X, R1, $R''_2$, $R''_3$, $R''_4$, $R''_5$, $R''_6$, $R''_7$, A, n, $R_8$ and $R_9$ are as previously defined,
said monoalkylation step being followed by a step of cleaving the sulfonyl group $R_{19}$ of the compound (Va) in order to obtain the compound of general formula (V), the compound (V) being a direct precursor of the compound of general formula (Ia), said compound (Ia) forming the radical (I) within the peptide $C^\alpha$-amide of the invention.

According to a second advantageous embodiment of the invention, the process for preparing the compound (Ia) is characterized in that it comprises:
a step of mono-N-alkylation of a compound of general formula (Ma):

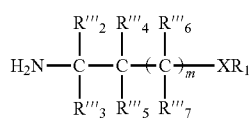

(IIIa)

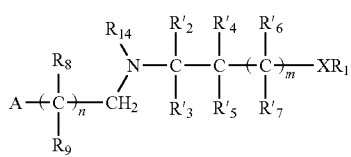

(VIIIb)

in which X, $R_1$ and m are as previously defined, one of $R'''_2$, $R'''_3$, $R'''_4$, $R'''_5$, $R'''_6$ or $R'''_7$ represents a reactive group comprising a reactive chemical function optionally protected with a protective group, said function being preferably chosen from the group comprising —COOH, —$NH_2$ and —OH, and making it possible to graft said compound (Ma) onto the solid support as mentioned above according to a method known to those skilled in the art for Fmoc SPPS, said optional protective group being preferably chosen from a group comprising tert-butyl, tert-butyloxycarbonyl, phenacyl, benzyl, benzyloxycarbonyl, methyl, ethyl, trityl and allyl, the others of said $R'''_2$, $R'''_3$, $R'''_4$, $R'''_5$, $R'''_6$ or $R'''_7$ which do not represent said reactive group have the same meaning as said $R_2$, $R_3$, $R_4$, $R_5$, $R_6$ or $R_7$ as previously defined and which do not represent —B—C-D, in order to obtain a compound of general formula (VIII):

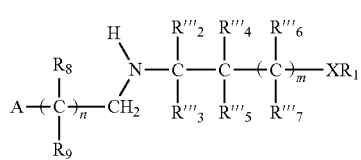

(VIII)

in which X, $R_1$, m, $R'''_2$, $R'''_3$, $R'''_4$, $R'''_5$, $R'''_6$, $R'''_7$, n, $R_8$, $R_9$ and A are as previously defined, a step of N-acylation or of protection of the secondary amine function of the compound of formula (VIII) in order to obtain a compound of general formula (VIIIa):

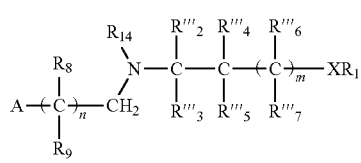

(VIIIa)

in which $R_{14}$=$R_{13}$ as previously defined or $R_{14}$ represents a protected aminoacyl residue of formula $R_{13}$—Xaa- with Xaa representing an amino acid residue, the possible reactive functions of the side chain of the amino acid residue Xaa being protected with protective groups normally used by those skilled in the art during SPPS, an optional step of deprotection of the reactive function included in one of said R''', so as to give a compound of general formula (VIIIb)

a step of grafting the compound (VIIIb) onto a solid support of formula:

H-E-O—C-D', H-E-NH—C-D' or Cl—C-D in which E, C and D' are as previously defined and H, O, NH and Cl correspond to the chemical symbols normally used, in order to obtain the compound of formula (Vb):

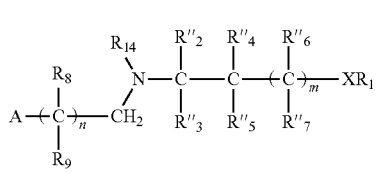

(Vb)

in which

X, $R_1$, m, $R''_2$, $R''_3$, $R''_4$, $R''_5$, $R''_6$, $R''_7$, $R_{14}$, n, $R_8$, $R_9$ and A are as previously defined, in the case where $R_{14}$=$R_{13}$, said grafting step being followed by a step of cleaving the $R_{14}$ group of the compound (Vb) in order to obtain a compound of general formula (V) as previously defined, said compound (V) being a direct precursor of a compound of formula (Ia) as previously defined, in the case where $R_{14}$=$R_{13}$-Xaa-, said grafting step being followed by a step of cleaving the $R_{13}$ group which is part of the $R_{14}$ group of the compound (Vb) in order to obtain a compound of general formula (Vc),

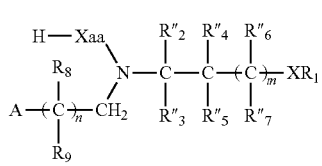

(Vc)

said compound (Vc) being the precursor of a peptide $C^\alpha$-amide of the invention comprising a radical (I), by elongation of the peptide chain by SPPS.

A subject of the invention is also a compound characterized in that it has general formula (Ia):

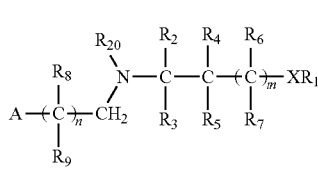

(Ia)

in which:

X, $R_1$, m, $R_2$, $R_3$, $R_4$, $R_5$, $R_6$, $R_7$, n, $R_8$, $R_9$ and A are as previously defined and $R_{20}$ represents a hydrogen or $R_{14}$.

A subject of the invention is also a process for preparing a peptide $C^\alpha$-amide of formula (II) as defined above by Fmoc SPPS, characterized in that it comprises a step of elongation, by Fmoc SPPS, of the compound (Ia) as previously defined, said elongation step making it possible to add Peptide1 as previously defined.

Advantageously according to the invention, the attachment of the first amino acid to the compound (Ia) by N-acylation (namely the addition of an amino acid to the nitrogen of the compound (Ia)), may be carried out very easily by virtue of the actual structure of the compound (Ia).

Indeed, the use of the compound of the invention (Ia) is extremely advantageous, compared, for example, with the compound (h) of the prior art defined in FIG. 5-1, since it is the original structure of said compound (Ia) which makes it possible to facilitate this step of N-acylation of the secondary amine.

A subject of the present invention is also a process for preparing a peptide $C^\alpha$-thioester of general formula (IX):

in which:

R'— represents a radical originating from a thiol of formula R'—SH, and Peptide1 is as previously defined, characterized in that it comprises a reaction for thioesterification between:

the peptide $C^\alpha$-amide of formula (II) as previously defined in which $R_1$=H, and
a thiol of formula R'—SH,
in order to obtain:
the peptide $C^\alpha$-thioester of formula (IX) as defined above, and
the compound of formula (Ib):

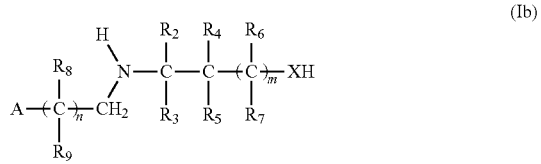

in which:
X, m, $R_2$, $R_3$, $R_4$, $R_5$, $R_6$, $R_7$, n, $R_8$, $R_9$ and A are as previously defined.

The compound (Ib) corresponds to the compound of general formula (Ia) in which $R_1$ and $R_{20}$ each represent a hydrogen atom.

The R'— radical originating from the thiol of formula R'—SH may represent any radical which makes it possible to form a thiol (R'—SH) when it is bonded to the SH function of the thiol.

The R'— radical may, for example, represent an alkyl, aryl, arylalkyl, cycloalkyl, heterocycloalkyl or heteroaryl group as defined above, it being possible for each of said groups to also comprise one or more conventional substituents chosen from: halogen, carboxyl, sulfonate, ammonium, alcohol, ether, alkyl, cycloalkyl, heterocycloalkyl, aryl, heteroaryl, alkoxy, haloalkyl, arylalkyl, heteroarylalkyl and arylheterocycloalkyl.

By way of example of an alkyl radical, mention may be made of one of those chosen from the group comprising ethyl, 2-hydroxyethyl, 3-hydroxypropyl, $NaSO_3CH_2CH_2$—, $HOOC$—$CH_2CH_2$—, $HOOC$—$CH_2$— or $CH_3CH_2COOCH_2CH_2$—.

By way of example of an aryl or arylalkyl radical, mention may be made of one of those chosen from the group comprising benzyl ($C_6H_5$—$CH_2$—), 4-methoxybenzyl (p-MeO-$C_6H_5$—$CH_2$—), 2,4,6-trimethoxybenzyl, 4-methylbenzyl, phenyl ($C_6H_5$—), p-(HOOC—$CH_2$)—$C_6H_4$—, p-$CF_3$—$C_6H_4$—, p-F—$C_6H_4$—, p-$C_5$-$C_6H_4$—, p-Br—$C_6H_4$—, p-I—$C_6H_4$—, p-$NO_2$—$C_6H_4$—, p-Me-$C_6H_4$— and p-HO—$CH_2$—$C_6H_4$—.

The reaction between the peptide $C^\alpha$-amide of formula (II) and the thiol R'—SH may be carried out in the presence of an excess of thiol in trifluoroacetic acid (TFA), acetic acid or formic acid or in an aqueous buffer, optionally with an organic cosolvent, urea or guanidinium chloride added thereto, so as to ensure the solubilization of the peptide $C^\alpha$-amide of formula (II) or of the thiol R'—SH.

The pH of the aqueous buffer may be from 0 to 8 and preferably from 1 to 4.

By way of example of an organic cosolvent, mention may be made of one of those chosen from the group comprising acetonitrile (MeCN), methanol (MeOH), isopropanol (iPrOH), dimethylformamide (DMF) and N-methyl-2-pyrrolidone (NMP).

Preferably, the reaction may be carried out in a 7:3 waterMeCN mixture, in the presence of 0.1% vv TFA and of 50 equivalents of a thiol R'SH.

In one particular mode of preparation of a peptide $C^\alpha$-thioester of formula (IX), D represents a solid support suitable for Fmoc SPPS and C is absent or represents an arm that can be used for Fmoc SPPS and preferably an arm that is stable with respect to TFA, such as the PAM or MBHA arm. In this particular mode, the peptide $C^\alpha$-thioester of formula (IX) is obtained by means, firstly, of a treatment of the peptidyl resin with TFA in order to cleave the protective groups of the side chains of Peptide1 that were used during the step in which Peptide1 was elongated by Fmoc SPPS, without detaching it from the solid support. Then, secondly, the thioesterification of the supported deprotected peptide obtained after the treatment with TFA is carried out by means of the thiol R'—SH. This also has the effect of detaching the peptide $C^\alpha$-thioester of formula (IX) from the solid support.

Advantageously according to the invention, the peptide $C^\alpha$-amide as defined above may be used to prepare a peptide $C^\alpha$-thioester. A subject of the invention is therefore also the use of a peptide $C^\alpha$-amide as defined above, for preparing a peptide $C^\alpha$-thioester.

The invention also relates to a process for preparing a peptide of general formula (X):

in which:

Peptide1 is as previously defined,

Yaa is an amino acid residue originating from an amino acid of formula H-Yaa-OH chosen from the group comprising a cysteine, a homocysteine, a β-mercaptovaline, a β-mercaptoleucine, a β-mercaptoisoleucine, a β-mercaptophenylalanine, a β-mercaptolysine, a β-mercaptoproline, a γ-mercaptovaline, a γ-mercaptoisoleucine, a γ-mercaptoleucine, a γ-mercaptolysine, a γ-mercaptoproline, or an amino acid substituted on its nitrogen atom $N^a$ with a group containing a β- or γ-aminothiol function, said group being chosen from the group comprising:

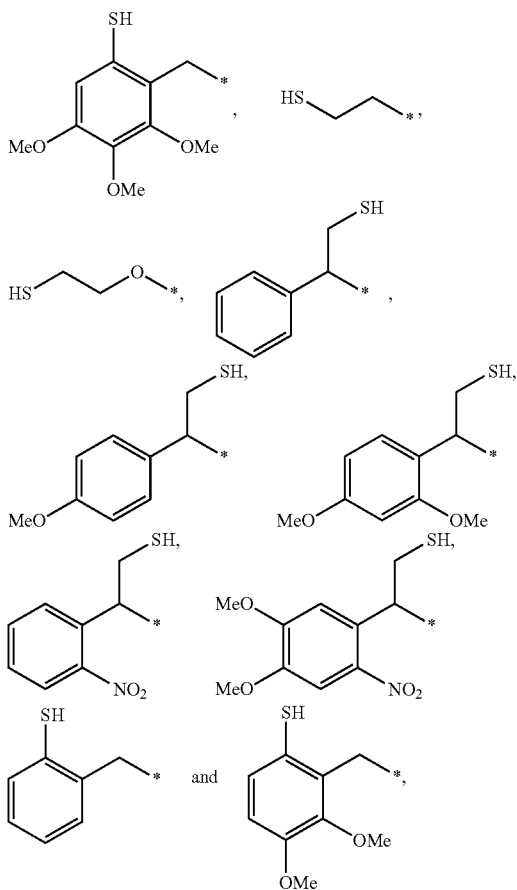

Peptide2=(Xaa)$_l$, with l=an integer ranging from 1 to 60, preferably from 4 to 40, Xaa represents, independently of one another, an amino acid residue originating from an amino acid of formula H—Xaa-OH, and when l is greater than or equal to 2, each of said Xaa is connected to its neighbor Xaa via a peptide bond, $R_{15}$ represents —OH, —NH$_2$ or a radical of general formula (I) as defined above, in which X=S and $R_1$ is a protective group for sulfur which is stable with respect to treatment with TFA and stable under NCL conditions, characterized in that:

a peptide C$^\alpha$-amide of general formula (II) as defined above, in which R1=H or a group which is labile under NCL native chemical ligation conditions, is reacted, by means of an NCL reaction, with a peptide possessing an N-terminal β- or γ-aminothiol residue of general formula (XI):

in which Yaa, $R_{15}$ and Peptide2 are as defined above, in order to obtain the peptide of general formula (X) as defined above and the compound of formula (Ia) as defined above.

Advantageously according to the invention, the peptide C$^\alpha$-amides have crypto-thioester properties and, in this regard, can therefore be used directly in an NCL native chemical ligation reaction, without being converted beforehand to peptide C$^\alpha$-thioesters. A subject of the invention is therefore also the use of a peptide C$^\alpha$-amide as defined above, in an NCL native chemical ligation reaction for preparing a peptide or a protein, in particular of therapeutic interest.

A subject of the present invention is also a process for preparing a peptide of general formula (XII):

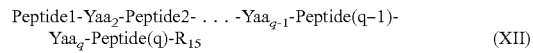

in which:

$R_{15}$ is as previously defined, q is an integer ranging from 3 to 10, each Yaa (Yaa$_2$, ..., Yaa$_{q-1}$ and Yaa$_q$) represents, independently of the others, an amino acid residue as previously defined, each peptide of formula (XIII) above (Peptide2 ... Peptide(q−1) and Peptide(q)), except Peptide1, represents, independently of the others, (Xaa)$_l$ as previously defined with respect to Peptide2, characterized in that:

a peptide of formula (II) as previously defined, in which $R_1$=H or a group which is labile under NCL native chemical ligation conditions, is reacted, by means of a first NCL reaction, with a peptide of general formula (XIa):

in which:

Yaa$_2$ is equal to Yaa as previously defined, and Peptide2 is as previously defined, $R_{16}$ represents a radical of formula (I) in which $R_1$ represents a protective group which is stable under NCL conditions, in order to obtain a peptide of general formula (XIII)

in which:

Yaa$_2$, Peptide1, Peptide2 and $R_{16}$ are as previously defined, and a compound of formula (Ib) as previously defined.

The peptide of general formula (XIII) which exhibits the $R_{16}$ radical as previously defined is then subjected to a deprotection under the conditions known to those skilled in the art in order to obtain the peptide of general formula (XIIIa)

in which:

$R_{17}$ represents a radical of formula (I) in which $R_1$ represents a hydrogen.

The compound (XIIIa) thus obtained is:

either converted beforehand to a peptide thioester and then reacted with a peptide of general formula (XIb):

or directly reacted with the peptide of formula (XIb), by exploiting the crypto-thioester properties of the compound (XIIIa)

This successive assembly is iteratively continued, by repeating (q−3) times the successive NCL and deprotection steps as described above.

The final compound of general formula (XII) is obtained by means of a final assembly making it possible to add the Peptide(q).

This final assembly is carried out:

either in two steps, namely prior conversion to thioester and then reaction with a peptide of general formula (XIc):

or by direct reaction with said peptide of formula (XIc).

When q is an integer equal to 3, then the peptide of formula (XII) is represented by the following formula (XII):

Peptide1-Yaa$_2$-Peptide2-Yaa$_3$-Peptide3-R$_{15}$    (XII)

The compound of formula (XIa) is a peptide C$^\alpha$-amide which does not have crypto-thioester properties owing to the masking of its thiol function by an R$_1$ radical representing a protective group for sulfur which is stable with respect to treatment with TFA and stable under NCL conditions.

A preferred R$_1$ group of the radical (I) present in said compound (XIa) is more particularly a group chosen from the group comprising acetamidomethyl (Acm), trimethylacetamidomethyl (Tacm), benzamidomethyl (B am), allyloxycarbonylaminomethyl (Allocam), phthalimidomethyl (Pim), 2-(trimethylsilyl)ethyl, t-butyl (tBu), 2,4,6-trimethylbenzyl, quinolinylmethyl (Qm), diphenyl-4-pyridylmethyl, 1-adamantyl, benzyloxymethyl (BOM), 2-tetrahydropyranyl (Thp) and benzylthiomethyl.

According to one preferred embodiment of the process for preparing the peptide of general formula (XII), Peptide1 is grafted beforehand onto a hydrocompatible solid support, for instance a support chosen from the group comprising Pega®, Chemmatrix™, agarose, sepharose and controlled pore glass (CPG) microparticles. More particularly, Peptide1 is grafted onto a solid support via a linker which can be cleaved after the (q−1) steps of NCL native chemical ligation, said linker preferably being an N-terminal arm as described in document WO 2011058188. Other ligation reactions (optionally requiring other types of precursors) may also be combined with NCL in the same strategy of multiple ligations on a solid support from N toward C.

The invention will be understood more clearly in the light of the nonlimiting and purely illustrative examples which follow. FIGS. 6 to 26 make it possible to illustrate said examples below.

FIGS. 1 to 5, relating to the prior art, have been commented upon in the introduction of the present application.

FIG. 5-1 represents a scheme of the principle of the synthesis of peptide C$^\alpha$-β-mercapto-amides of type (e), detailing the difficult step of N-acylation of the secondary amine.

FIG. 5-2 is a comparison between the acylation of a secondary amine bearing a 2-hydroxybenzyl group (j) and that of a secondary amine bearing a 2-methoxybenzyl group (m), and illustrates more particularly the principle of the assistance, by a 2-hydroxybenzyl group, of the acylation of a secondary amine.

Figure 7:
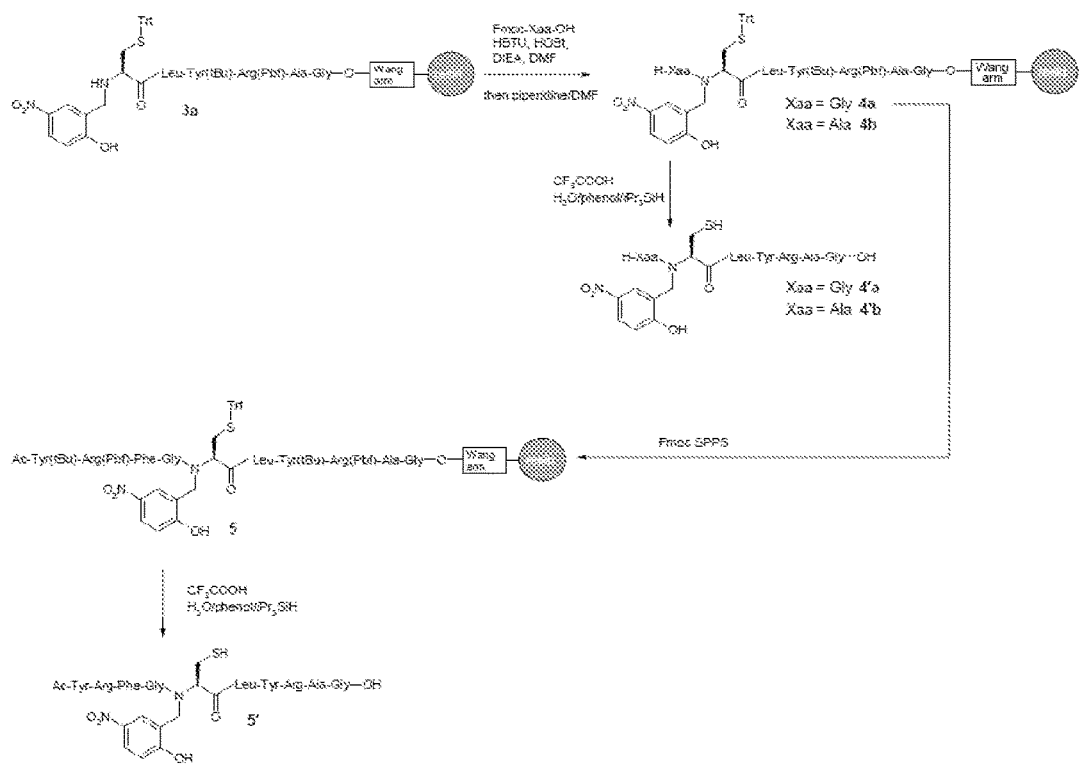

FIG. 7 is a synthesis scheme illustrating the preparation of a peptide C$^\alpha$-amide of general formula (II) (compounds 5 and 5') from a compound of general formula (Ia) (compound 3a).

Figure 1:
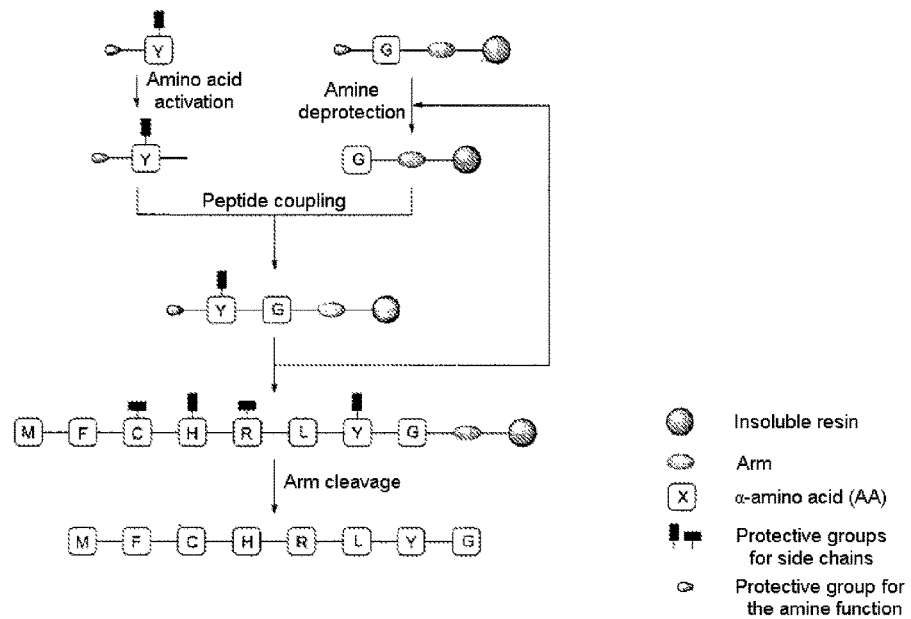
FIG. 1 represents the steps of solid phase peptide synthesis (SPPS).
Figure 2:
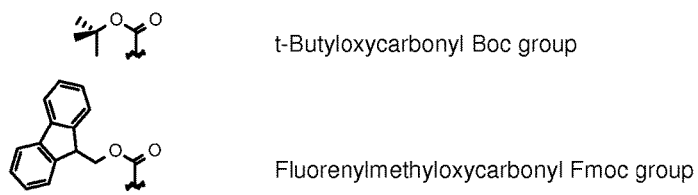
FIG. 2 represents the protective groups (Boc and Fmoc) for amines used in SPPS.
Figure 3:
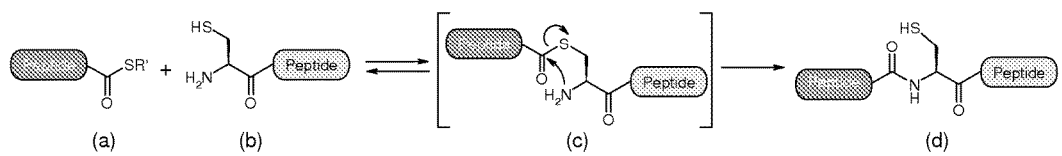
FIG. 3 represents an "NCL" native chemical ligation reaction between a peptide C$^\alpha$-thioster (compound (a)) and a peptide bearing an N-terminal cysteine (compound (b)).
Figure 4:
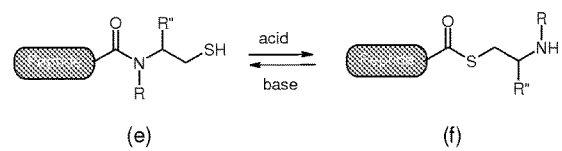
FIG. 4 represents the use of peptide C$^\alpha$-N-alkyl(or aryl)-N-(β-mercaptoalkyl)-amides (e) for:
the synthesis of peptide C$^\alpha$-thioesters (a) (by acyl transfer from N to S) (FIGS. 4-1 and 4-2),
direct use in NCL (FIG. 4-3).
Figure 4:
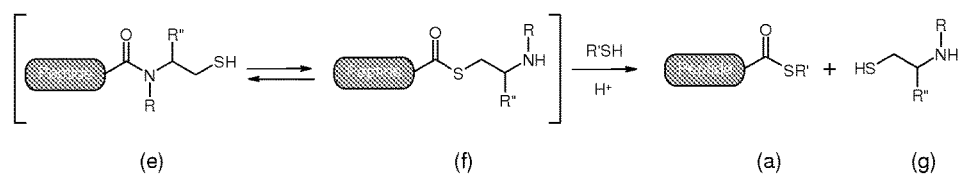
Figure 4:
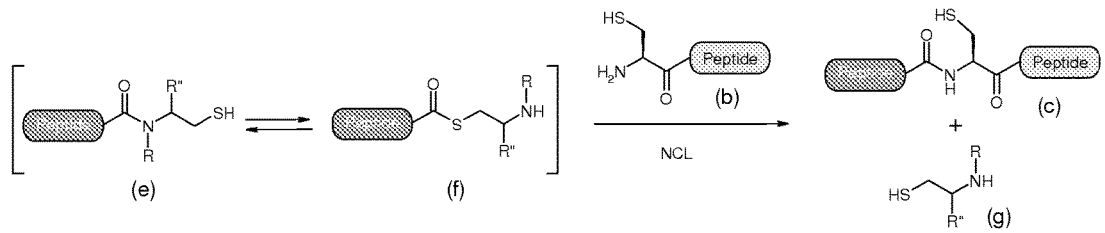
Figures 1, 5:
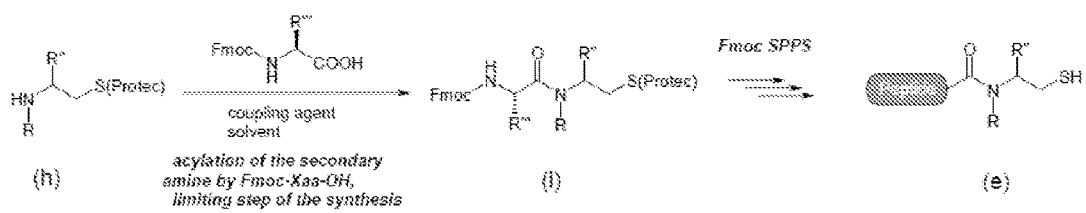
Figures 2, 5:
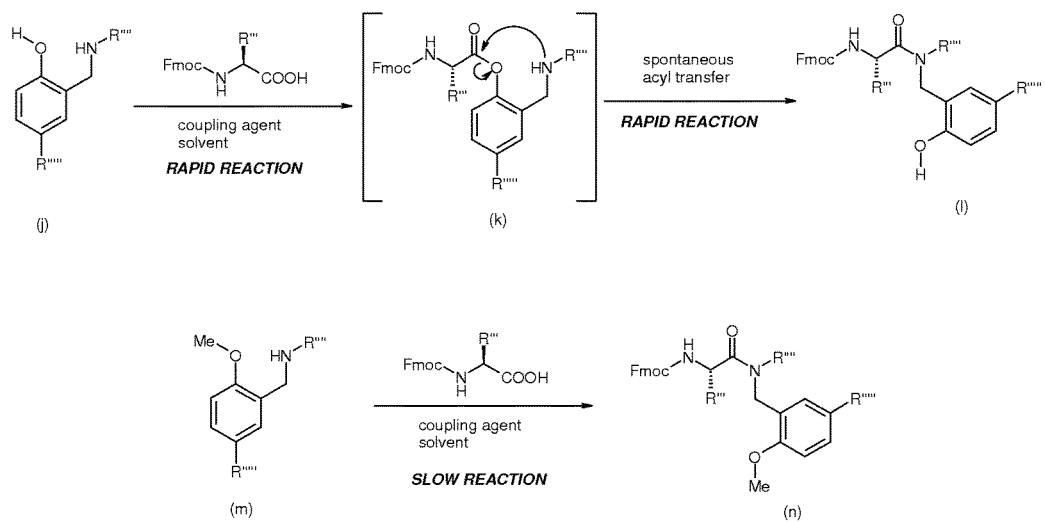
Figure 6:
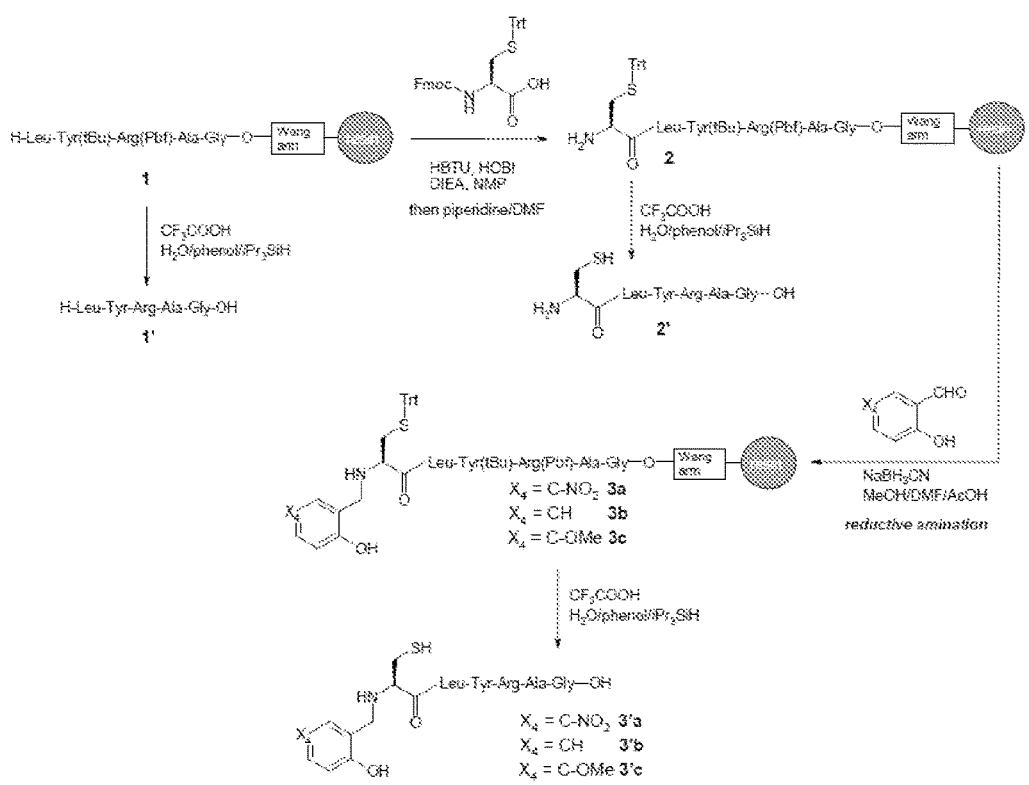
FIG. 6 is a synthesis scheme illustrating the preparation of six compounds of the invention corresponding to general formula (Ia) (compounds 3a, 3b, 3c, 3'a, 3'b and 3'c).
Figure 8:
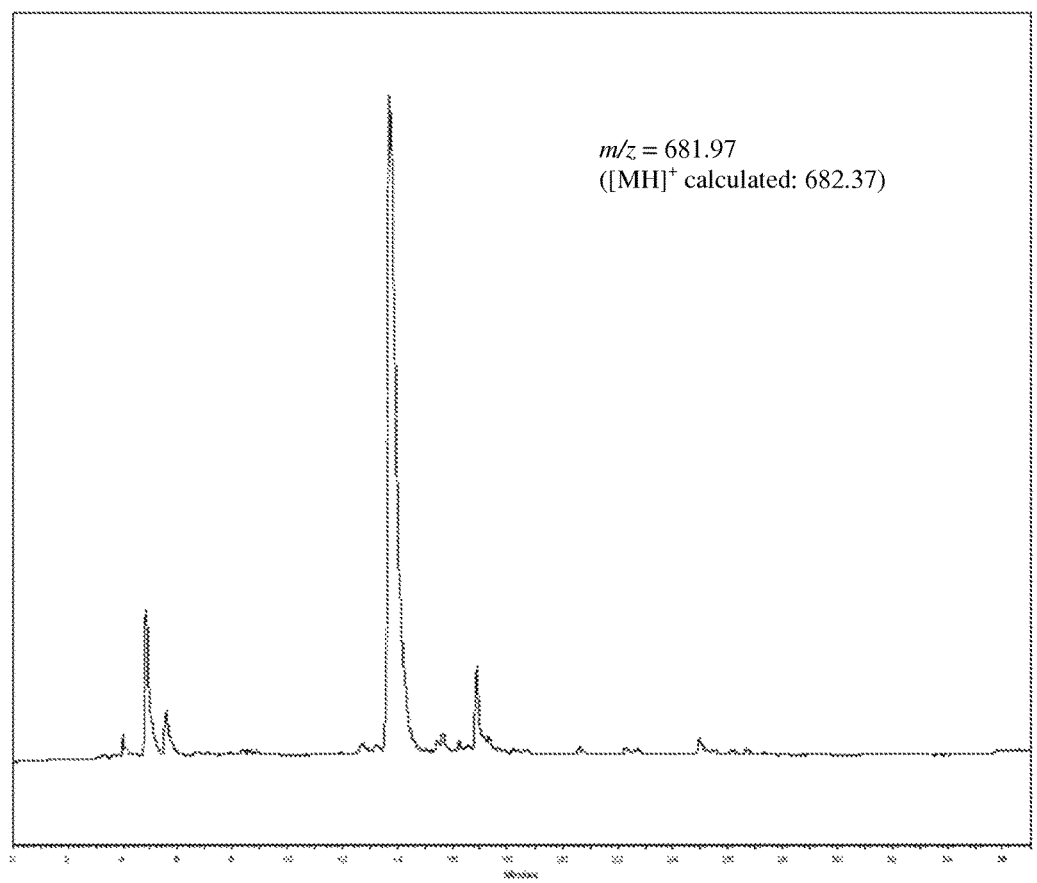

FIG. 8 represents the chromatogram of an HPLC/MS analysis of the peptide 2' represented in FIG. 6.

Figure 9:
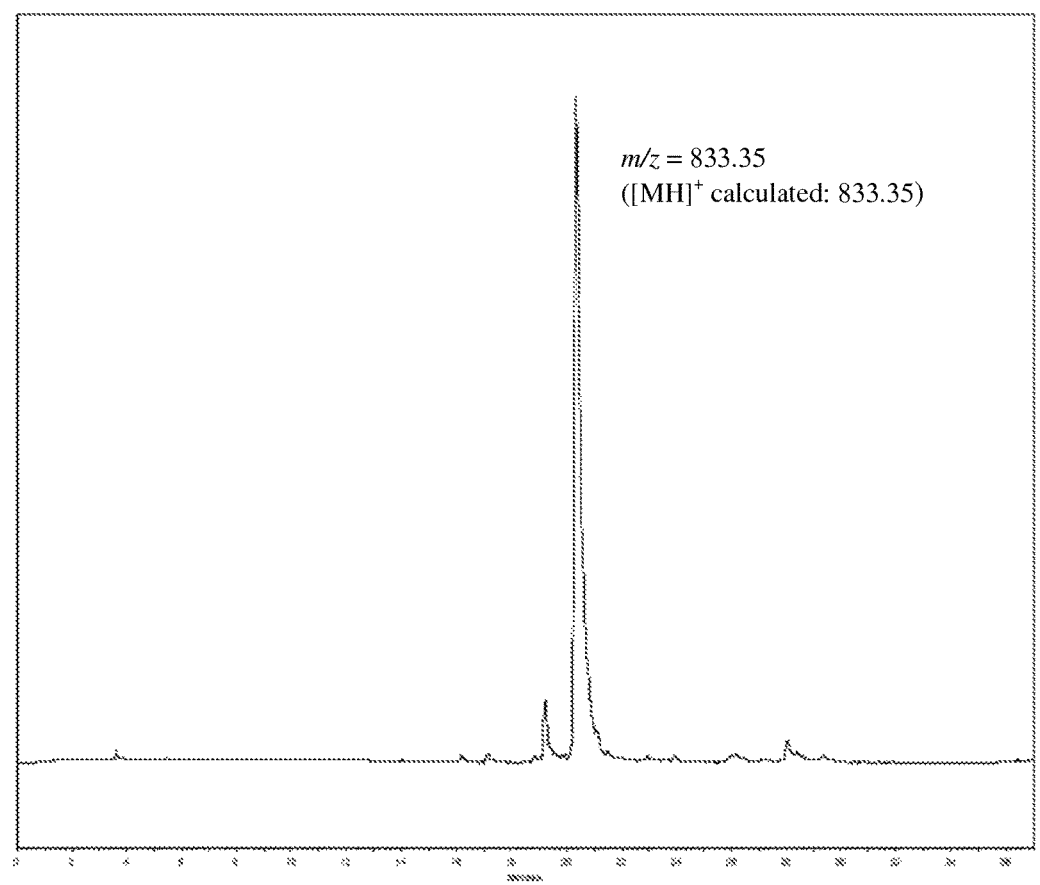
Figure 10:
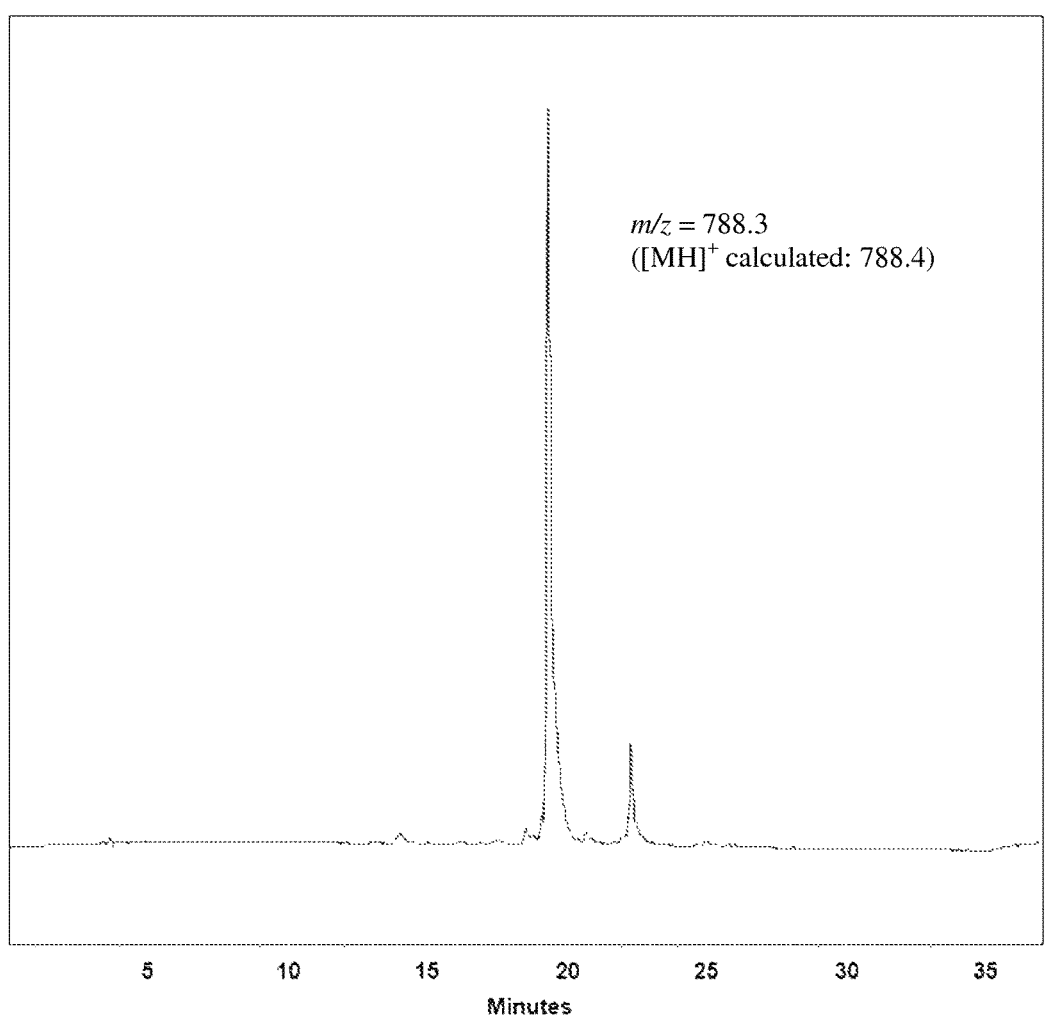
Figure 11:
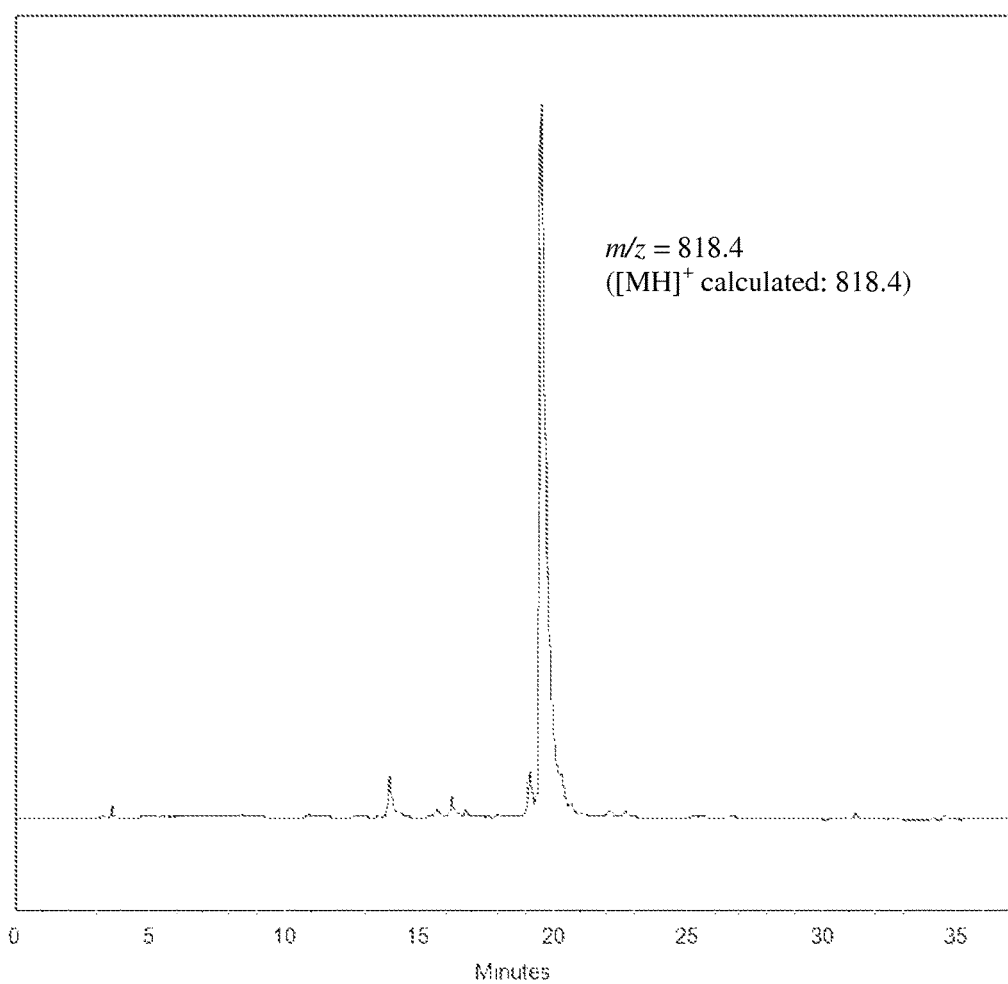

FIGS. 9, 10 and 11 represent the chromatograms of respective HPLC/MS analyses of the peptides 3'a, 3'b and 3'c represented in FIG. 6.

Figure 12:
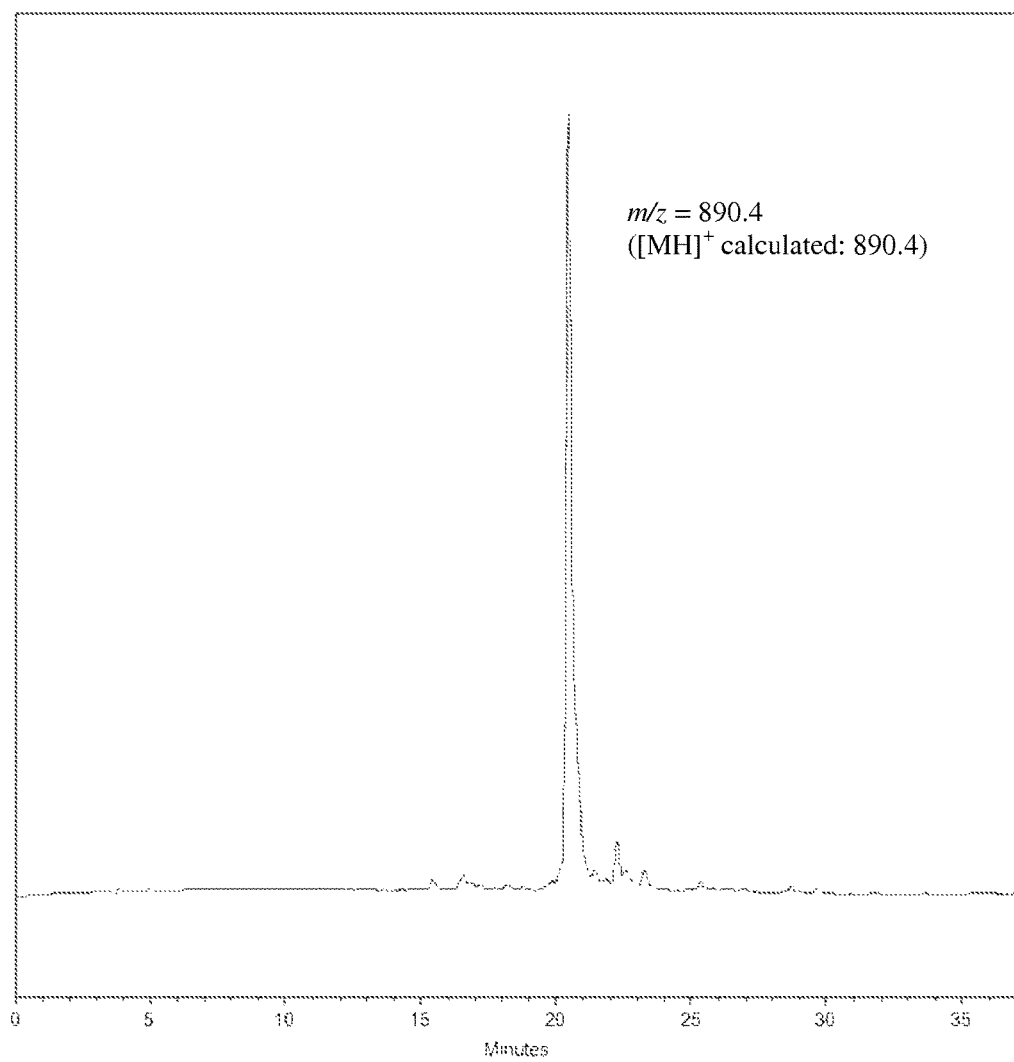
Figure 13:
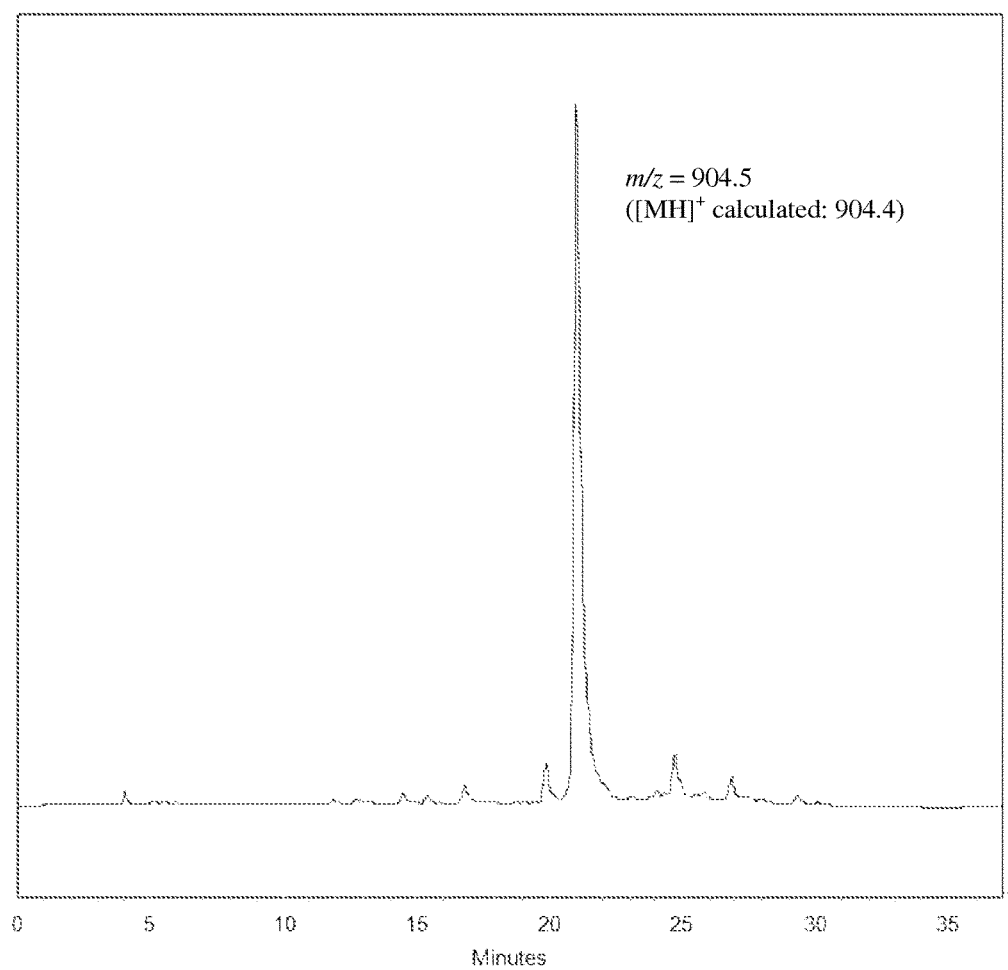

FIGS. 12 and 13 represent the chromatograms of respective HPLC/MS analyses of the peptides 4'a and 4'b represented in FIG. 7.

Figure 14:
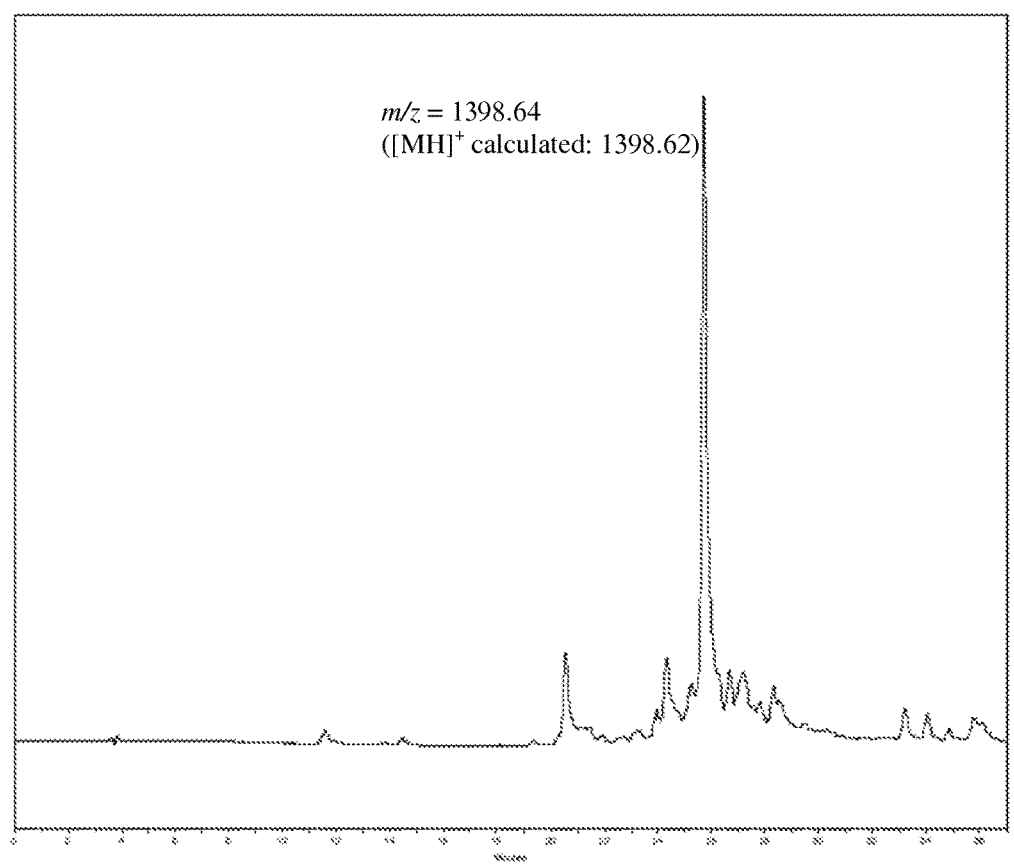

FIG. 14 represents the chromatogram of an HPLC/MS analysis of the peptide 5' represented in FIG. 7.

Figure 15:
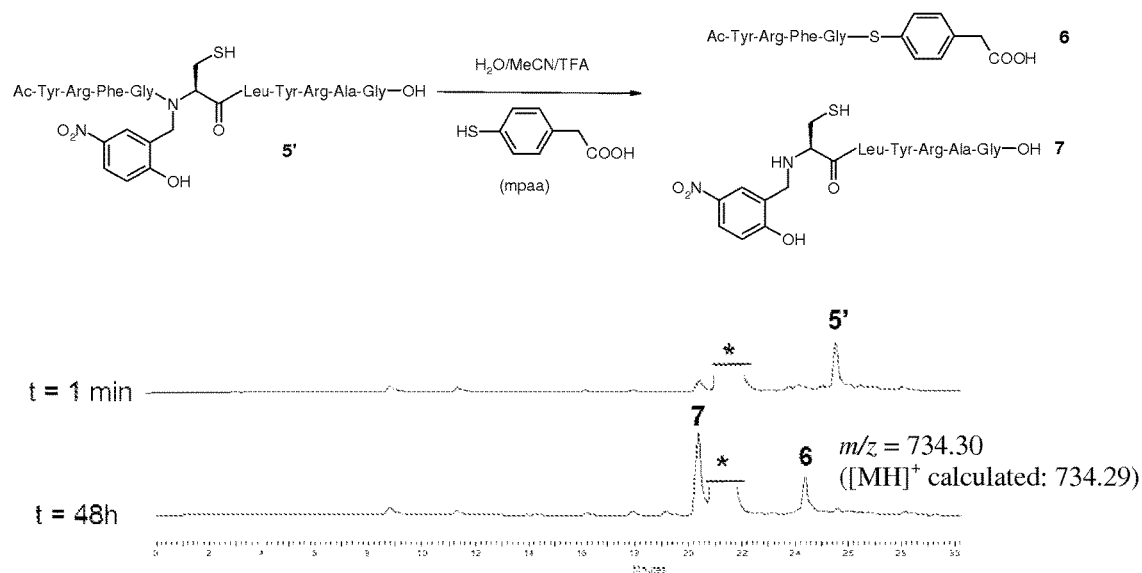

FIG. 15 represents the use of a peptide C$^\alpha$-amide of general formula (II) (compound 5') for obtaining a peptide C$^\alpha$-thioester (compound 6).

Figure 16:
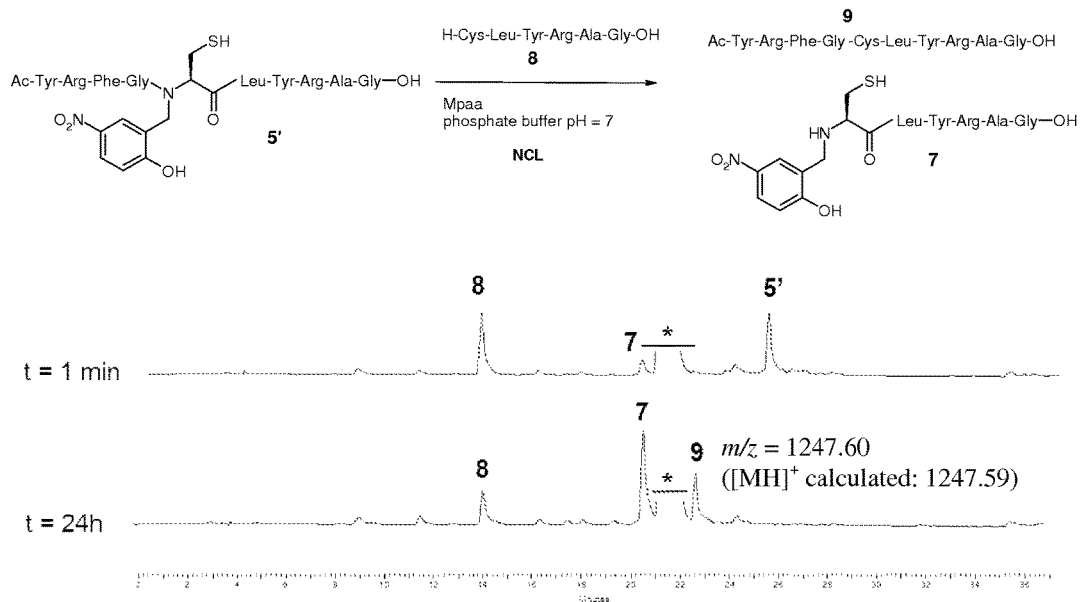

FIG. 16 represents the use of a peptide C$^\alpha$-amide of general formula (II) (compound 5') in an NCL reaction for obtaining a model peptide (compound 9) (reactivity of crypto-thioester type).

Figure 17:
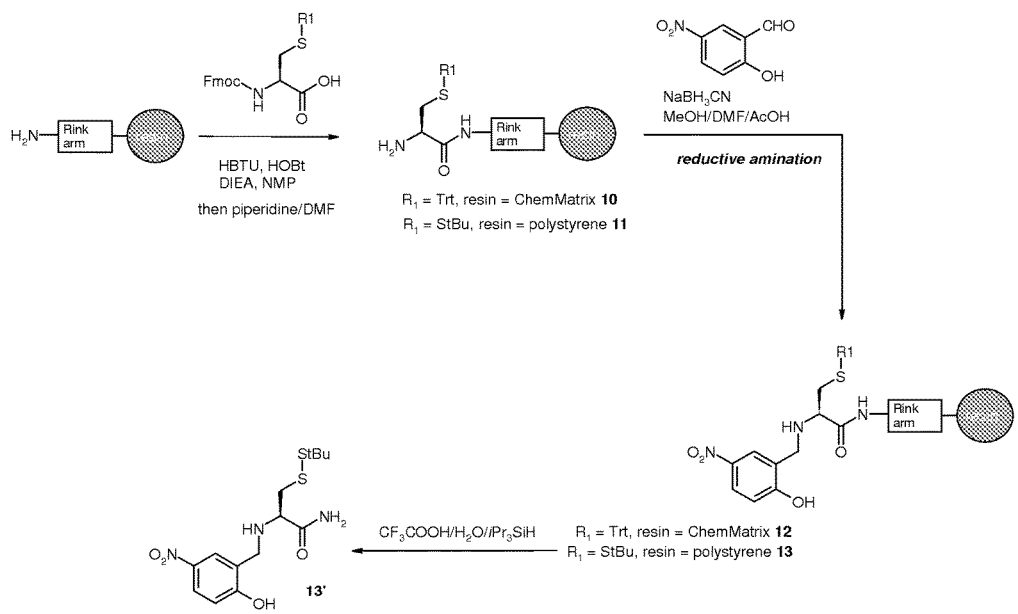

FIG. 17 is a synthesis scheme illustrating the preparation of three compounds of the invention corresponding to general formula (Ia) (compounds 12, 13 and 13').

Figure 18:
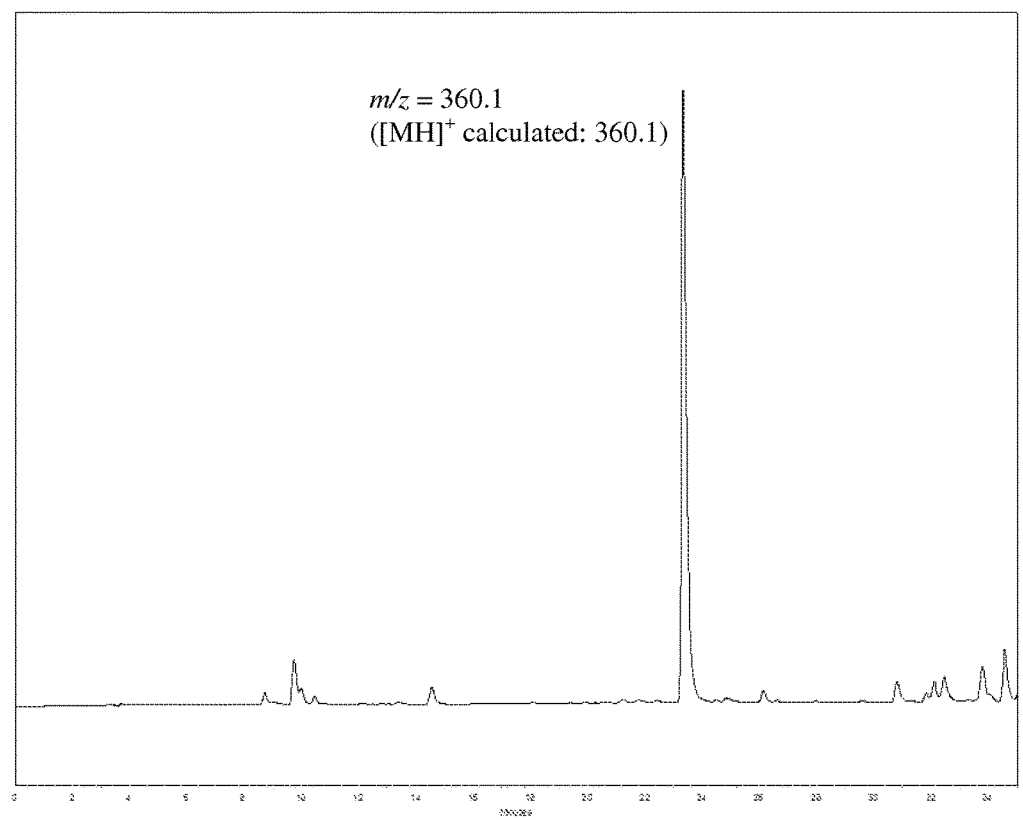

FIG. 18 represents the chromatogram of an HPLC/MS analysis of compound 13' represented in FIG. 17.

Figure 19:
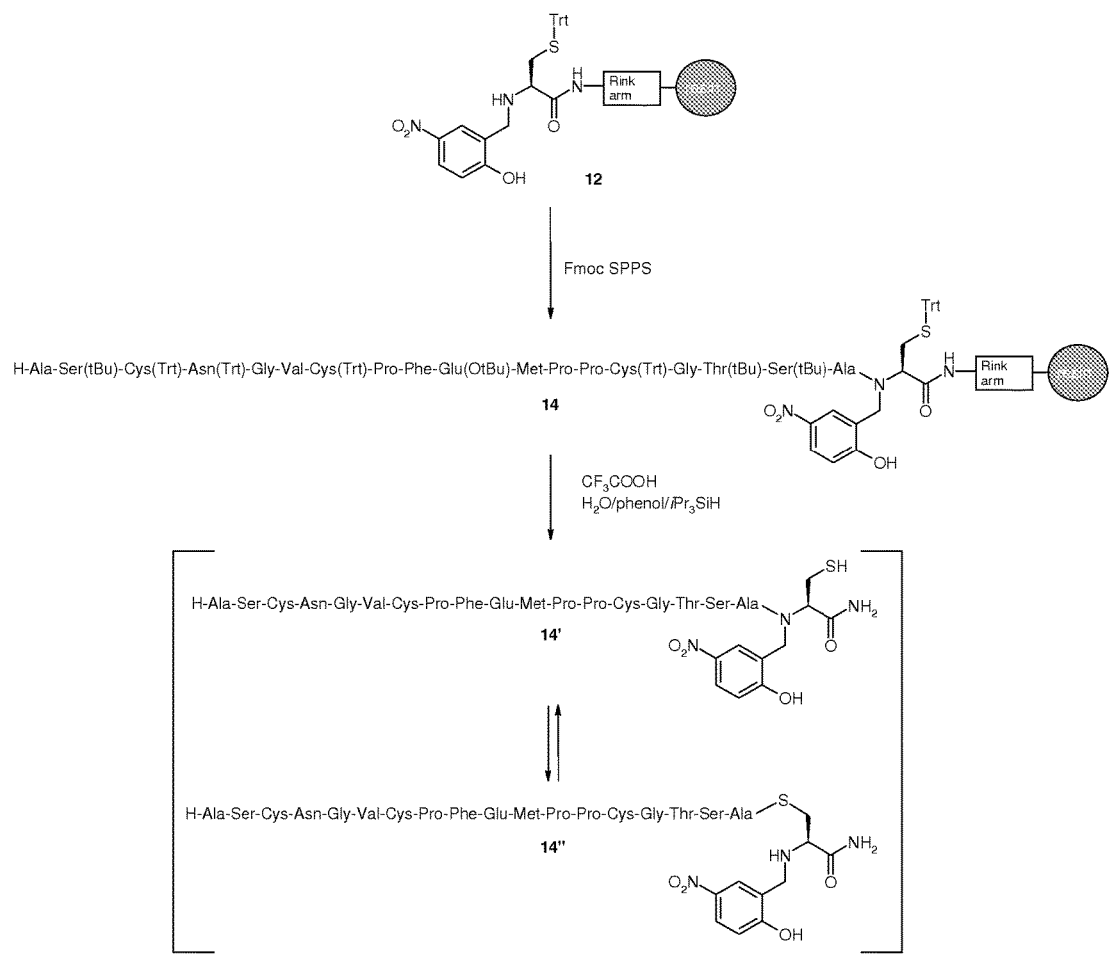

FIG. 19 is a synthesis scheme illustrating the preparation of a peptide C$^{er}$-amide of general formula (II) (compounds 14 and 14') from a compound of general formula (Ia) (compound 12).

Figure 20:
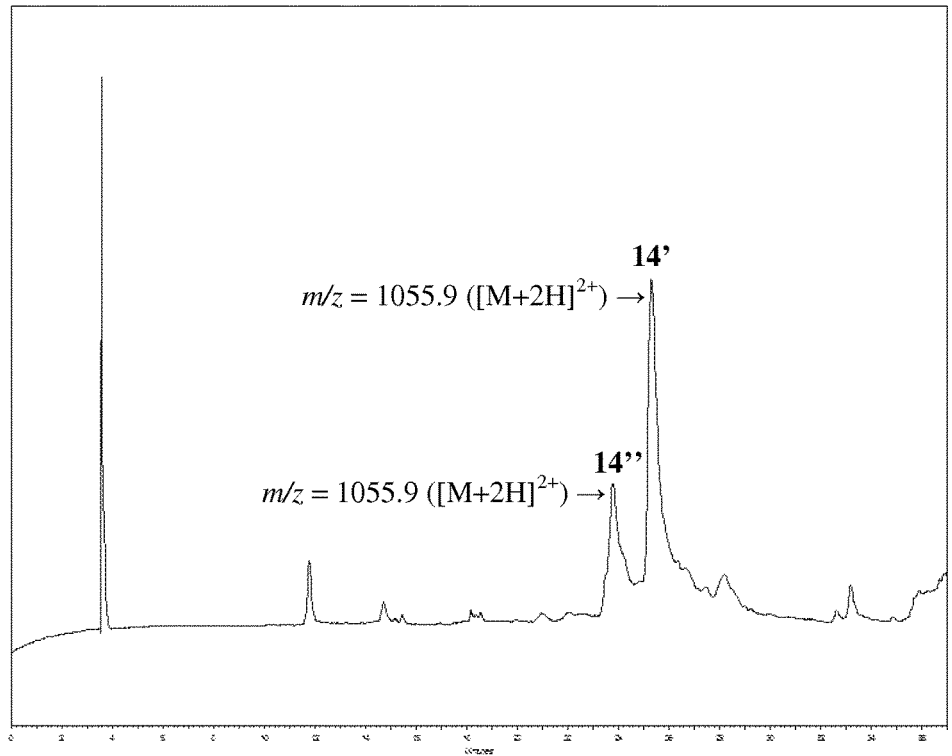

FIG. 20 represents the chromatogram of an HPLC/MS analysis of the peptides 14' and 14" represented in FIG. 19.

Figure 21:
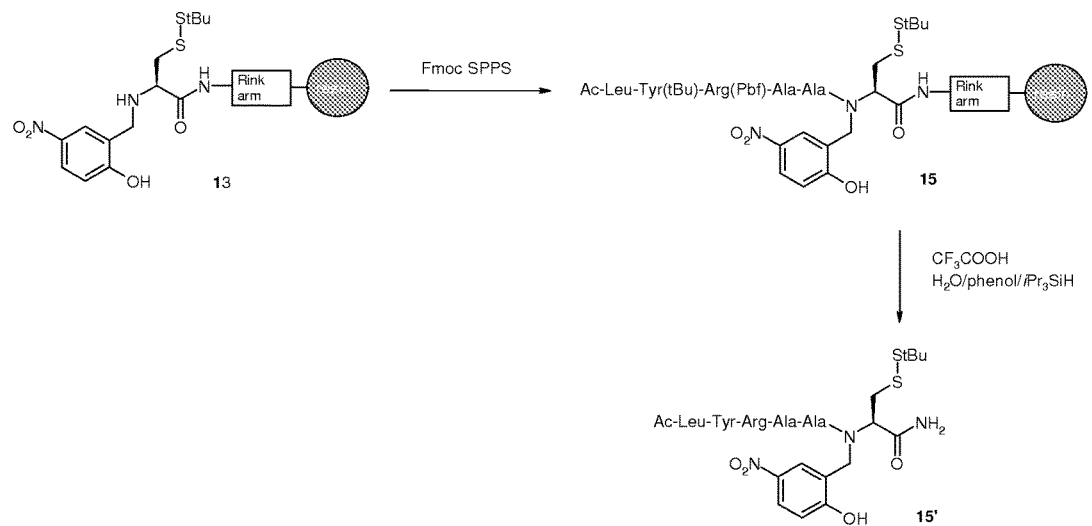

FIG. 21 is a synthesis scheme illustrating the preparation of a peptide C$^{er}$-amide of general formula (II) (compounds 15 and 15') from a compound of general formula (Ia) (compound 13).

Figure 22:
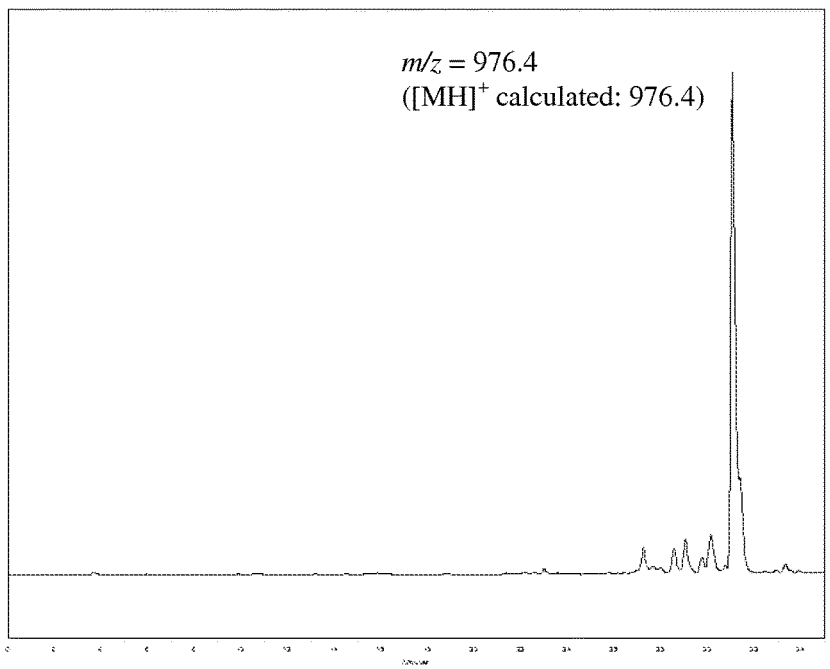

FIG. 22 represents the chromatogram of an HPLC/MS analysis of the peptide 15' represented in FIG. 21.

Figure 23:
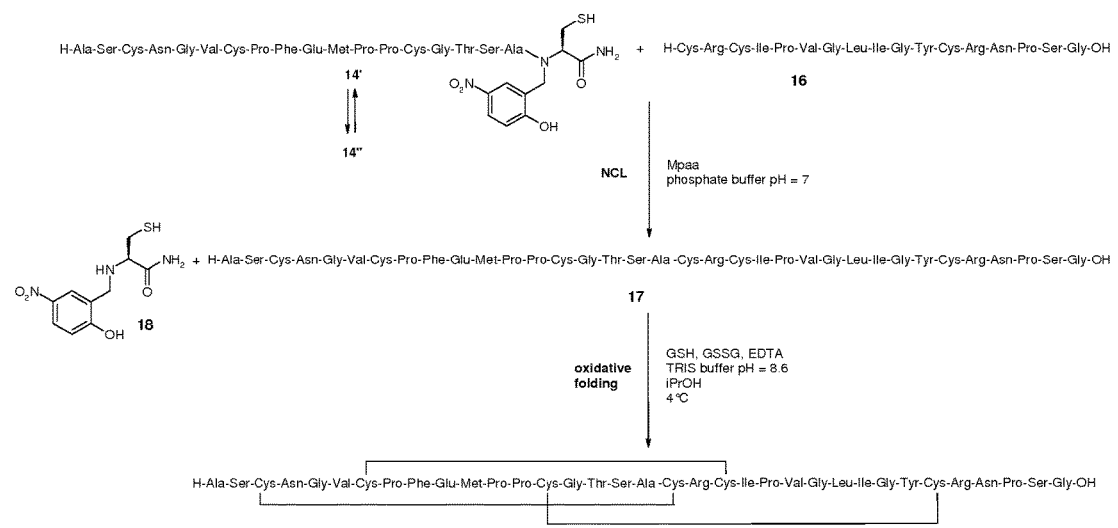

FIG. 23 represents the use of the peptides 14'/14" in an NCL native chemical ligation reaction so as to give a peptide 17, followed by a one-pot oxidative folding in order to obtain a peptide 19.

Figure 24:
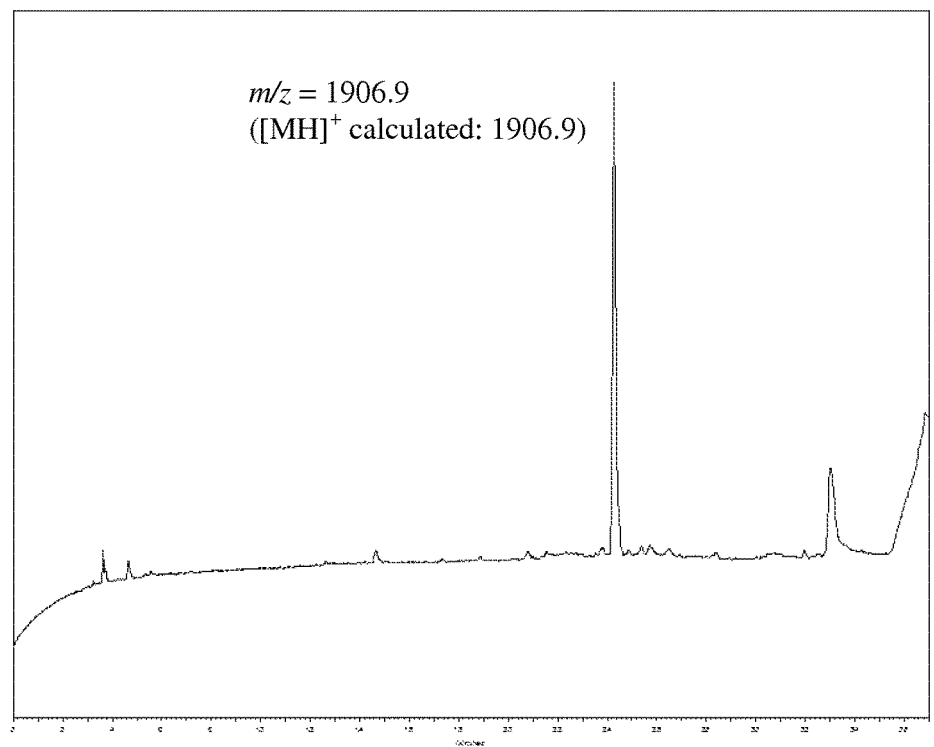

FIG. 24 represents the chromatogram of an HPLC/MS analysis of the peptide 16 represented in FIG. 23.

Figure 25:
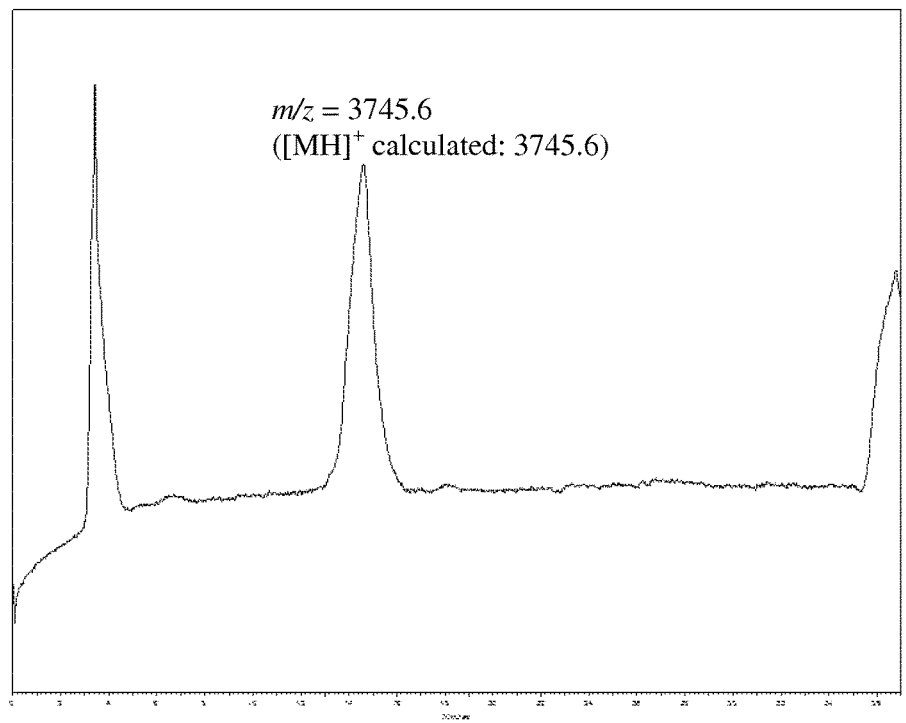

FIG. 25 represents the chromatogram of an HPLC/MS analysis of the peptide 17 represented in FIG. 23.

Figure 26:
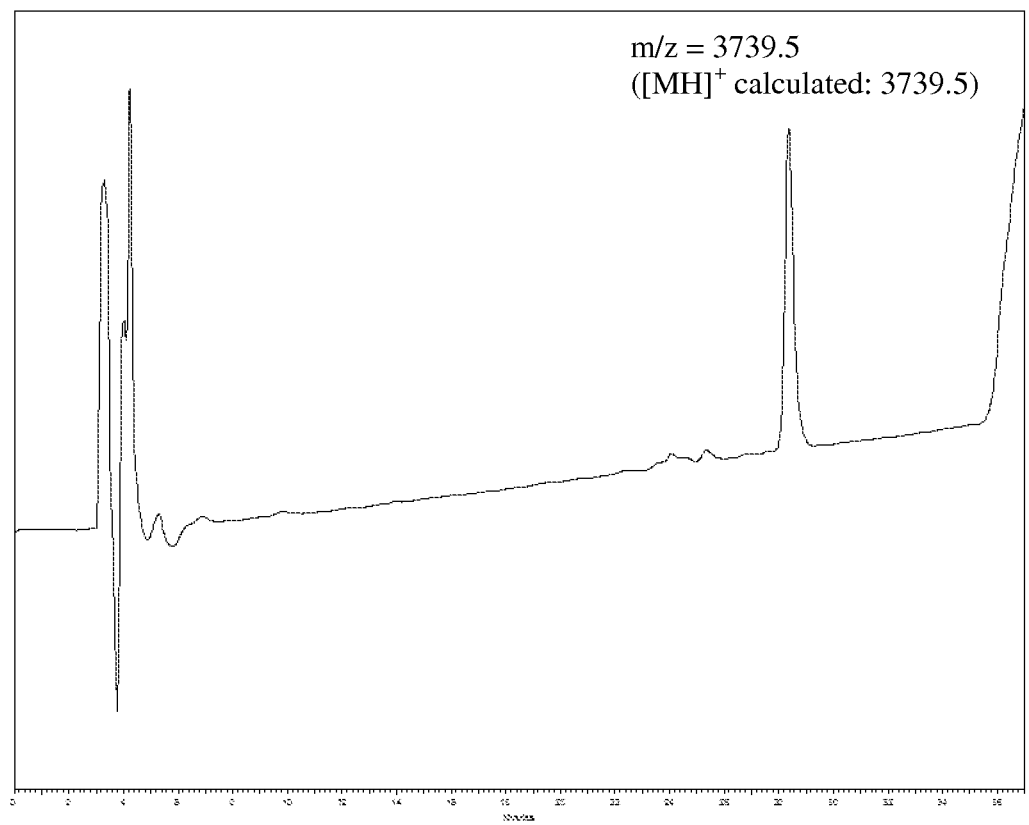

FIG. 26 represents the chromatogram of an HPLC/MS analysis of the peptide 19 represented in FIG. 23.

EXAMPLES

In examples 1 and 2 described below, in the radical of formula (I) or in the compound (Ia):
X represents a sulfur atom,
R$_1$ represents a hydrogen atom or a trityl (Trt) group,
R$_2$ represents a group —B—C—D in which:
  B represents —CO-Leu-Tyr-Arg-Ala-Gly-O—, C is absent and D represents a hydrogen atom, or
  B represents —CO-Leu-Tyr(t-Bu)-Arg(Pbf)-Ala-Gly-O—, C represents a Wang arm (—CH$_2$—C$_6$H$_4$—O—CH$_2$—) and D represents a solid support such as a resin of polystyrene type,
R$_3$, R$_4$ and R$_5$ each represent a hydrogen atom,
m is equal to n which is equal to 0,
A representing an aryl group of general formula:

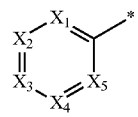

in which $X_1$ represents C—OH, each of $X_2$, $X_3$ and $X_5$ represents CH and $X_4$ represents CH, C—OCH$_3$ or C—NO$_2$, and, if it is the compound (Ia), $R_{20}$ represents a hydrogen atom.

When D represents a hydrogen atom, this means that the radical (I) is not attached to a solid support. In this case, $R_1$ represents H and $R_2$ represents a group —B—C-D in which B represents —CO-Leu-Tyr-Arg-Ala-Gly-O—, C is absent and D represents a hydrogen atom.

When D represents a solid support, this means that the radical (I) is attached to said solid support (said solid support being an integral part of the definition of the radical (I)). In this case, $R_1$ represents trityl (Trt) and $R_2$ represents a group —B—C-D in which B represents —CO-Leu-Tyr(t-Bu)-Arg(Pbf)-Ala-Gly-O—, C represents a Wang arm (—CH$_2$—C$_6$H$_4$—O—CH$_2$—) and D represents a solid support such as a resin of polystyrene type.

The products obtained were analyzed by HPLC on a column: nucleosil C18 300 Å 5 μm, 4.6×250 mm, gradient: 5-50% MeCNH$_2$O+0.1% TFA over the course of 30 min, flow rate: 1 mlmin, followed by UV detection (λ=276 nm or 360 nm) and then MALDI-TOF mass spectrometry.

Example 1

Preparation of a Peptide C$^\alpha$-Amide of General Formula (II)

1) Synthesis of a Compound of General Formula (Ia)

The synthesis of a compound of general formula (Ia) is illustrated in FIG. 6. Compounds 3a, 3b, 3c and 3'a, 3'b and 3'c correspond to general formula (Ia) in which:

for compounds 3a, 3b and 3c, X represents S, $R_1$ represents Trt, $R_3$, $R_4$ and $R_5$ represent H, m is equal to n which is equal to 0, $R_{20}$ represents a hydrogen atom, $R_2$ represents -CO-Leu-Tyr(t-Bu)-Arg(Pbf)-Ala-Gly-O-[Wang arm]-[Resin], and A represents respectively:

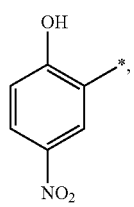
(3a)

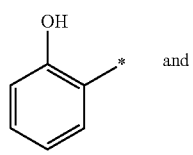
and
(3b)

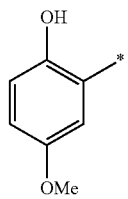
(3c)

for compounds 3'a, 3'b and 3'c, X represents S, $R_1$ represents H, $R_3$, $R_4$ and $R_5$ represent H, m is equal to n which is equal to 0, $R_{20}$ represents a hydrogen atom, $R_2$ represents —CO-Leu-Tyr-Arg-Ala-Gly-OH, and A represents respectively:

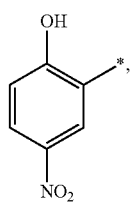
(3'a)

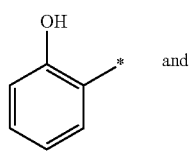
and
(3'b)

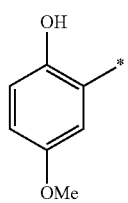
(3'c)

Synthesis of the Peptidyl Resin 2

The synthesis scheme is illustrated in FIG. 6.

Compound 1 corresponds to the formula H-E-O—C-D' as defined above in which:
E represents Leu-Tyr(t-Bu)-Arg(Pbf)-Ala-Gly,
C represents a Wang arm and D' represents a resin of polystyrene type.

Compound 2 corresponds to general formula (IVa) as defined above:

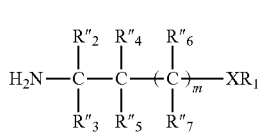
(IVa)

in which
X represents S, $R_1$ represents Trt, $R''_3$, $R''_4$, $R''_5$, $R''_6$ and $R''_7$ represent H, m is equal to 0, and $R''_2$ represents:

-CO-Leu-Tyr(t-Bu)-Arg(Pbf)-Ala-Gly-O-[Wang arm]-[Resin]

The peptidyl resin 2 of formula:

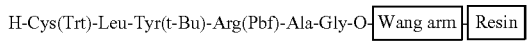

was synthesized under standard conditions (ABI 433 synthesizer, Fastmoc program). An aliquot of resin is treated for 2 h with 87.5:5:5:2.5 CF$_3$COOHphenolH$_2$Otri-isopropylsilane so as to detach and deprotect the peptide 2 in order to obtain the peptide 2', which is precipitated by dilution in a 1:1 petroleum ether/Et$_2$O mixture, washed (Et$_2$O), dried, and then analyzed by HPLC and mass spectrometry (see FIG. 8).

Peptide 2' (see FIG. 8):
Empirical formula: C$_{29}$H$_{47}$N$_9$O$_8$S;
HPLC: t$_R$=14.41 min (C18, gradient: 5-50% MeCNH$_2$O+ 0.1% TFA over the course of 30 min);
UV detection (λ=276 nm);
MS (MALDI-TOF): m/z observed=682.0 ([MH]$^+$ calculated for C$_{29}$H$_{47}$N$_9$O$_8$S=682.3).

Reductive Aminations
The synthesis scheme is illustrated in FIG. 6.
0.1 mmol of the peptidyl resin 2 of formula:

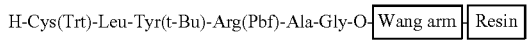

is solvated in the mixture dimethylformamide/methanolacetic acid (9:9:2).

10 equivalents of aldehyde (of general formula VII) as represented in FIG. 6 are then dissolved in 4 ml of dimethylformamide/methanol (1:1) and are added to the peptidyl resin 2. The resulting suspension is stirred for 45 minutes. The resin is then washed with the dimethylformamide/methanol mixture (1:1).

20 equivalents of NaBH$_3$CN are dissolved in 4 ml of dimethylformamide/methanolacetic acid (9:9:2) and then added to the resin. The resulting suspension is stirred for 30 minutes. The resin is washed with the dimethylformamide/methanolacetic acid mixture (9:9:2). An aliquot of resin is treated for 2 h with 87.5:5:5:2.5 TFA/PhOH/H$_2$O/i-Pr$_3$SiH so as to detach and deprotect the peptide 3a, 3b or 3c in order to obtain respectively the peptide 3'a, 3'b or 3'c, which is precipitated by dilution in a 1:1 petroleum ether/Et$_2$O mixture, washed (Et$_2$O), dried and then analyzed by HPLC and mass spectrometry (see FIGS. 9, 10 and 11).

Peptide 3'a (FIG. 9):
Empirical formula: C$_{36}$H$_{52}$N$_{10}$O$_{11}$S;
HPLC: t$_R$=20.44 min (C18, gradient: 5-50% MeCNH$_2$O+ 0.1% TFA over the course of 30 min);
UV detection (λ=360 nm);
MS (MALDI-TOF): m/z observed=833.3 ([M1-1]$^+$ calculated for C$_{36}$H$_{52}$N$_{10}$O$_{11}$S=833.4).

Peptide 3'b (FIG. 10):
Empirical formula: C$_{36}$H$_{53}$N$_9$O$_9$S;
HPLC: t$_R$=19.17 min (gradient: 5-50% MeCNH$_2$O+0.1% TFA over the course of 30 min);
UV detection (λ=276 nm);
MS (MALDI-TOF): m/z obtained=788.3 ([MH]$^+$ calculated for C$_{36}$H$_{53}$N$_9$O$_9$S=788.4).

Peptide 3'c (FIG. 11):
Empirical formula: C$_{37}$H$_{55}$N$_9$O$_{10}$S;
HPLC: t$_R$=19.59 min (C18, gradient: 5-50% MeCNH$_2$O+ 0.1% TFA over the course of 30 min);
UV detection (λ=276 nm);
MS (MALDI-TOF): m/z obtained=818.4 ([MH]$^+$ calculated for C$_{37}$H$_{55}$N$_9$O$_{10}$5=818.4).

2) Synthesis of a Peptide C$^\alpha$-Amide of General Formula (II)

The synthesis of a peptide C$^\alpha$-amide of general formula (II) is illustrated in FIG. 7. Compounds 5 and 5' correspond to general formula (II) in which:
for compound 5, X represents S, R$_1$ represents Trt, R$_3$, R$_4$ and R$_5$ represent H, Peptide1 represents Ac-Tyr(tBu)-Arg(Pbf)-Phe-Gly, m is equal to n which is equal to 0, R$_2$ represents

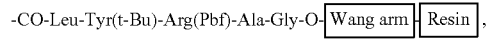

and A represents

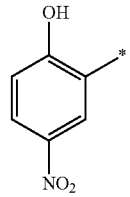 [SMILES: *c1cc([N+](=O)[O-])ccc1O]

for compound 5', X represents S, R$_1$ represents H, R$_3$, R$_4$ and R$_5$ represent H, Peptide1 represents Ac-Tyr-Arg-Phe-Gly-, m is equal to n which is equal to 0, R$_2$ represents —CO-Leu-Tyr-Arg-Ala-Gly-OH, and A represents:

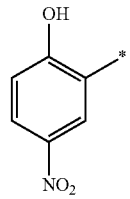 [SMILES: *c1cc([N+](=O)[O-])ccc1O]

Coupling of Fmoc-Glycine onto the Supported N-Alkyl Cysteine 3a

The coupling of Fmoc-glycine onto the peptidyl resin 3a is illustrated in FIG. 7.

The coupling of Fmoc-glycine onto the peptidyl resin 3a is carried out under standard conditions (ABI 433, Fastmoc program). The peptidyl resin 3a is solvated in DMF. 10 equivalents of protected amino acid (Fmoc-Gly-OH as represented in FIG. 7) are then activated with 10 equivalents of HBTU O-benzotriazole-N,N,N',N'-tetramethyluronium hexafluorophosphate) in the presence of 10 equivalents of HOBt (1-hydroxybenzotriazole) and 20 equivalents of DIEA (diisopropylethylamine) and then added to the resin, which is then stirred for 30 minutes at ambient temperature. The resin is rinsed with DMF and CH$_2$Cl$_2$ and then the Fmoc group is cleaved using piperidine (20% in NMP), three successive treatments of five minutes each. The resin is rinsed with DMF and CH$_2$Cl$_2$. An aliquot of resin 4a thus obtained is treated for 2 h with 87.5:5:5:2.5 TFA/PhOH/ H$_2$O/i-Pr$_3$SiH so as to detach and deprotect the peptide 4a and to obtain the peptide 4'a, which is analyzed by HPLC and mass spectrometry (FIG. 12).

Peptide 4'a (FIG. 12):

Molecular formula: $C_{38}H_{55}N_{11}O_{12}S$;

HPLC: $t_R$=20.53 min (C18, gradient: 5-50% MeCNH$_2$O+ 0.1% TFA over the course of 30 min);

UV detection ($\lambda$=276 nm);

MS (MALDI-TOF): m/z obtained=890.4 ([MH]$^+$ calculated for $C_{38}H_{55}N_{11}O_{12}S$=890.4).

Coupling of Fmoc-Alanine onto the Supported N-Alkyl Cysteine 3a

The coupling of Fmoc-alanine onto the peptidyl resin 3a is illustrated in FIG. 7.

The peptidyl resin 3a is solvated in DMF. 10 equivalents of protected Fmoc-alanine (Fmoc-Ala-OH as represented in FIG. 7) are then activated with 10 equivalents of HBTU in the presence of 10 equivalents of HOBt and 20 equivalents of DIEA in DMF and of the peptidyl resin 3a for 30 minutes at ambient temperature. This step is carried out twice. The resin is rinsed with DMF and DCM and then the amine is deprotected with piperidine (20% in NMP), three times for five minutes. The resin is rinsed with DMF and DCM. An aliquot of resin 4b thus obtained is treated for 2 h with 87.5:5:5:2.5 TFA/PhOH/H$_2$O/i-Pr$_3$SiH so as to detach and deprotect the peptide 4b and to obtain the peptide 4'b, which is analyzed by HPLC and mass spectrometry (FIG. 13).

Peptide 4'b (FIG. 13):

Molecular formula: $C_{39}H_{57}N_{11}O_{12}S$;

HPLC: $t_R$=21.50 min (gradient: 5-50% MeCNH$_2$O+0.1% TFA over the course of 30 min DAD detection);

UV detection ($\lambda$=276 nm);

MS (MALDI-TOF): m/z obtained=904.5 ([MFI]$^+$ calculated for $C_{39}H_{57}N_{11}O_{12}S$=904.4).

Elongation of the Peptide 5' Using the Compound 4a Obtained

The elongation of the peptide 5' is represented in FIG. 7.

The continuation of the elongation of the peptide is carried out under standard conditions (ABI 433, Fastmoc program) with the peptidyl resin 4a. An aliquot of resin 5 is treated for 2 h with 87.5:5:5:2.5 TFA/PhOH/H$_2$O/i-Pr$_3$SiH so as to obtain the peptide 5' which is precipitated by dilution in a 1:1 petroleum ether/Et$_2$O mixture, washed (Et$_2$O), dried and then analyzed by HPLC and mass spectrometry (FIG. 14).

Peptide 5' (FIG. 14):

Molecular formula: $C_{39}H_{57}N_{11}O_{12}S$;

HPLC: $t_R$=21.50 min (gradient: 5-50% MeCNH$_2$O+0.1% TFA over the course of 30 min DAD detection);

UV detection ($\lambda$=276 nm);

MS (MALDI-TOF): m/z obtained=904.5 ([MH]$^+$ calculated for $C_{39}H_{57}N_{11}O_{12}S$=904.4).

Example 2

Use of the Peptide C$^\alpha$-Amide of General Formula (II)

1) in a Thioesterification Reaction in an Acidic Medium

The use of a peptide C$^\alpha$-amide 5' of general formula (II) in a thioesterification reaction is illustrated in FIG. 15.

2.5 µmol of peptide 5' (peptide of general formula (II)) and 100 µmol of mercaptophenylacetic acid (namely a thiol of general formula R'—SH with R' representing pHOOC—CH$_2$—C$_6$H$_4$— as represented in FIG. 15) are dissolved in 1 ml of the mixture H$_2$OMeCN (7:3)+0.1% TFA. The reaction mixture is stirred for 48 hours at ambient temperature. The progression of the reaction is monitored by HPLC (FIG. 15).

The desired peptide C$^\alpha$-thioester of formula 6 and compound 7 corresponding to general formula (Ia) in which:

X represents S, R$_1$ represents H, R$_3$, R$_4$ and R$_5$ represent H, R$_{20}$ represents H, m is equal to n which is equal to 0, R$_2$ represents —CO-Leu-Tyr-Arg-Ala-Gly-OH, and A represents:

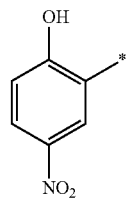 [SMILES: *c1cc([N+](=O)[O-])ccc1O]

are thus obtained.

This compound of formula (Ia) is particularly advantageous owing to its characteristic absorption in the ultraviolet range ($\lambda$max~400-450 nm): HPLC analysis with detection in this wavelength range makes it possible to easily detect it and characterize it, which will also allow those skilled in the art to conclude that the peptide C$^\alpha$-thioester of formula (IX) as defined above has indeed been formed.

Peptide C$^\alpha$-thioester 6 (FIG. 15):

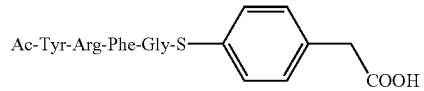

2) in an NCL Native Chemical Ligation Reaction

The use of a peptide C$^\alpha$-amide 5' of general formula (II) in a native chemical ligation reaction is illustrated in FIG. 16.

The peptide C$^\alpha$-amide of general formula (II) (compound 5'), by virtue of its crypto-thioester properties, can be used directly in an NCL native chemical ligation reaction, without converting it beforehand to the peptide C$^\alpha$-thioester (FIG. 16).

2.5 µmol of crude crypto-thioester peptide 5' and 1.5 equivalents of cysteinyl peptide 8 are dissolved in 1 ml of degassed solution containing 50 mM of mercaptophenylacetic acid, 20 mM of triscarboxyethylphosphine and 200 mM of phosphate buffer, pH=7. The reaction mixture is stirred for 24 h at 37° C. under argon.

A peptide 9 and a compound 7 of general formula (Ia) are thus obtained.

Peptide 9 (FIG. 16): Ac-Tyr-Arg-Phe-Gly-Cys-Leu-Tyr-Arg-Ala-Gly-OH

In examples 3 and 4 described below, in the radical of formula (I) or in the compound (Ia):

X represents a sulfur atom,

R$_1$ represents a hydrogen atom, a trityl (Trt) group, or a tert-butylsulfanyl (StBu) group, R$_2$ represents a group —B—C-D in which:

B represents —CO—NH—, where

C is absent and D represents a hydrogen atom, or

C represents a Rink arm (—CH[2,4-di-MeO-C$_6$H$_4$]-C$_6$H$_4$—O—CH$_2$—CO—NH—CH$_2$) and D represents a solid support such as a resin of ChemMatrix or polystyrene type, R$_3$, R$_4$ and R$_5$ each represent a hydrogen atom, m is equal to n which is equal to 0, A representing an aryl group of general formula:

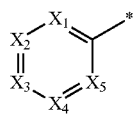

in which $X_1$ represents C—OH, each of $X_2$, $X_3$ and $X_5$ represents CH and $X_4$ represents C—$NO_2$, and, if it is the compound (Ia), $R_{20}$ represents a hydrogen atom.

When D represents a hydrogen atom, this means that the radical (I) is not attached to a solid support. In this case, $R_1$ represents H or a tert-butylsulfanyl (StBu) group and $R_2$ represents a group —B—C-D in which B represents —CO—NH—, C is absent and D represents a hydrogen atom.

When D represents a solid support, this means that the radical (I) is attached to said solid support (said solid support being an integral part of the definition of the radical (I)). In this case, $R_1$ represents a trityl (Trt) group or a tert-butylsulfanyl (StBu) group and $R_2$ represents a group —B—C-D in which B represents —CO—NH—, C represents a Rink arm (—CH[2,4-di-MeO-$C_6H_4$]-$C_6H_4$—O—$CH_2$—CO—NH—) and D represents a solid support such as a resin of ChemMatrix or polystyrene type.

The products obtained were analyzed by HPLC on a column: nucleosil C18 300 Å 5 μm, 4.6×250 mm, gradient: 5-50% MeCN/$H_2O$+0.1% TFA over the course of 30 min, flow rate: 1 ml/min, followed by UV detection (λ=276 nm or 320 nm) and then by MALDI-TOF mass spectrometry.

Example 3

Preparation of Peptide $C^\alpha$-Amide of General Formula (II)

1) Synthesis of a Compound of General Formula (Ia)

The synthesis of a compound of general formula (Ia) is illustrated in FIG. 17.

Compounds 12, 13 and 13' correspond to general formula (Ia) in which:

for compounds 12 and 13, X represents S, $R_3$, $R_4$ and $R_5$ represent H, m is equal to n which is equal to 0, $R_{20}$ represents a hydrogen atom, $R_2$ represents

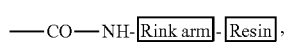

A represents:

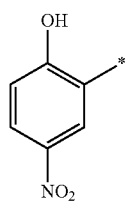

and $R_1$ represents Trt (12), or StBu (13), for compound 13', X represents S, $R_1$ represents StBu, $R_3$, $R_4$ and $R_5$ represent H, m is equal to n which is equal to 0, $R_{20}$ represents a hydrogen atom, $R_2$ represents —CO—$NH_2$, A represents:

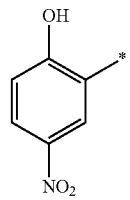

Synthesis of the Cysteinyl Resins 10 and 11

The synthesis scheme is illustrated in FIG. 17.

Compounds 10 and 11 correspond to general formula (IVa) as defined above:

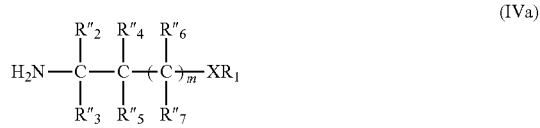

(IVa)

in which

X represents S, $R''_3$, $R''_4$, $R''_5$, $R''_6$ and $R''_7$ represent H, m is equal to 0, $R''_2$ represents

and $R_1$ represents Trt (10) or StBu (11).

The cysteinyl resins 10 and 11 of respective formula:

(10)

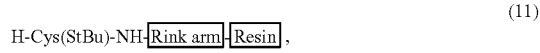

(11)

were synthesized under standard conditions (ABI 433 synthesizer, Fastmoc program).

Reductive Aminations

The synthesis scheme is illustrated in FIG. 17.

0.1 mmol of the peptidyl resin 10 or 11 as defined respectively above is solvated in the mixture dimethylformamide/methanol/acetic acid (9:9:2).

167 mg (10 equivalents) of 2-hydroxy-5-nitrobenzaldehyde dissolved in 4 ml of dimethylformamide/methanol (1:1) are added to the resin. The resulting suspension is stirred for 45 minutes. The resin is then washed with the dimethylformamide/methanol (1:1) mixture.

126 mg (20 equivalents) of $NaBH_3CN$ dissolved beforehand in 4 ml of dimethylformamide/methanolacetic acid (9:9:2) are added to the resin. The resulting suspension is stirred for 30 minutes. The resin is washed with the dimethylformamide/methanolacetic acid (9:9:2) mixture. An aliquot of the resin 13 is treated for 2 h with 92.5:5:2.5 TFA$H_2O$/i-$Pr_3$SiH in order to obtain the compound 13', which is analyzed by HPLC and mass spectrometry after evaporation of the TFA (see FIG. 18).

Compound 13' (FIG. 18):

Empirical formula: $C_{14}H_{21}N_3O_4S_2$;

HPLC: $t_R$=23.4 min (C18, gradient: 5-50% MeCNH$_2$O+ 0.1% TFA over the course of 30 min);

UV detection ($\lambda$=320 nm);

MS (ESI+): m/z observed=360.1 ([MH]$^+$ calculated for $C_{14}H_{22}N_3O_4S_2$=360.1).

2) Synthesis of a Peptide C$^\alpha$-Amide of General Formula (II)

The synthesis of a peptide C$^\alpha$-amide of general formula (II) is illustrated in FIG. 19. Compounds 14, 14', 15 and 15' correspond to general formula (II) in which:

for compound 14, X represents S, $R_1$ represents Trt, $R_3$, $R_4$ and $R_5$ represent H, Peptide1 represents H-Ala-Ser(tBu)-Cys(Trt)-Asn(Trt)-Gly-Val-Cys(Trt)-Pro-Phe-Glu(OtBu)-Met-Pro-Pro-Cys(Trt)-Gly-Thr(tBu)-Ser(tBu)-Ala-, m is equal to n which is equal to 0, $R_2$ represents —CO—NH-[Rink arm]-[Resin], and A represents:

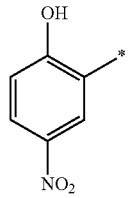

for compound 14', X represents S, $R_1$ represents H, $R_3$, $R_4$ and $R_5$ represent H, Peptide1 represents H-Ala-Ser-Cys-Asn-Gly-Val-Cys-Pro-Phe-Glu-Met-Pro-Pro-Cys-Gly-Thr-Ser-Ala-, m is equal to n which is equal to 0, $R_2$ represents —CO—NH$_2$, and A represents:

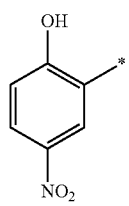

for compound 15, X represents S, $R_1$ represents StBu, $R_3$, $R_4$ and $R_5$ represent H, Peptide1 represents H-Leu-Tyr(tBu)-Arg(Pbf)-Ala-Gly-, m is equal to n which is equal to 0, $R_2$ represents —CO—NH-[Rink arm]-[Resin], and A represents

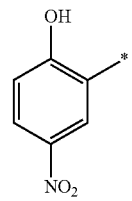 [SMILES: *c1cc([N+](=O)[O-])ccc1O]

for compound 15', X represents S, $R_1$ represents StBu, $R_3$, $R_4$ and $R_5$ represent H, Peptide1 represents H-Leu-Tyr(tBu)-Arg(Pbf)-Ala-Gly-, m is equal to n which is equal to 0, $R_2$ represents —CO—NH$_2$, and A represents:

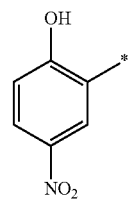 [SMILES: *c1cc([N+](=O)[O-])ccc1O]

Elongation of the Peptide 14' Using Compound 12

The elongation of the peptide 14' is represented in FIG. 19.

The elongation of the peptide is carried out under standard conditions (ABI 433, Fastmoc program, HCTU as coupling agent) with the resin 12, by carrying out twice in a row the coupling of the first amino acid Fmoc-Ala-OH before deprotecting the Fmoc group and continuing the elongation.

The peptidyl resin 14 obtained is treated for 2 h with 87.5:5:5:2.5 TFA/PhOH/H$_2$O/i-Pr$_3$SiH so as to obtain the peptide 14' which is precipitated by dilution in a 1:1 petroleum ether/Et$_2$O mixture, washed (Et$_2$O) and then dried under reduced pressure. The precipitate is taken up in demineralized water and lyophilized. It is then analyzed by HPLC and mass spectrometry (FIG. 21). The peptide amide 14' is obtained by mixing with the peptide thioester 14" (the two compounds are in equilibrium in solution).

Peptide 14' (FIG. 20):

Molecular formula: $C_{85}H_{126}N_{23}O_{31}S_5$;

HPLC: (gradient: 5-50% MeCNH$_2$O+0.1% TFA over the course of 30 min UV detection, $\lambda$=276 nm) $t_R$=25.3 min;

MS (ESI+): m/z obtained=1055.9 ([M+2H]$^{2+}$).

Peptide 14" (FIG. 20):

Molecular formula: $C_{85}H_{126}N_{23}O_{31}S_5$;

HPLC: $t_R$=23.8 min (gradient: 5-50% MeCNH$_2$O+0.1% TFA over the course of 30 min;

UV detection ($\lambda$=276 nm);

MS (ESI+): m/z obtained=1055.9 ([M+2H]$^{2+}$).

Elongation of the Peptide 15' Using Compound 13

The elongation of the peptide 15' is represented in FIG. 21.

The elongation of the peptide is carried out under standard conditions (ABI 433, Fastmoc program, HCTU as coupling agent) with the resin 13, by carrying out twice in a row the coupling of the first amino acid Fmoc-Ala-OH before deprotecting the Fmoc group and continuing the elongation.

The peptidyl resin 15 obtained is treated for 2 h with 97.5:5:5:2.5 TFA/i-Pr$_3$SiH so as to obtain the peptide 15' which is precipitated by dilution in a 1:1 petroleum ether/Et$_2$O mixture, washed (Et$_2$O), dried and then analyzed by HPLC and mass spectrometry (FIG. 21).

Peptide 15' (FIG. 22):
Molecular formula: $C_{43}H_{65}N_{11}O_{11}S_2$;
HPLC: $t_R$=31.0 min (gradient: 5-50% MeCN/H$_2$O+0.1% TFA over the course of 30 min);
UV detection ($\lambda$=320 nm);
MS (MALDI-TOF): m/z obtained=976.4 ([MH]$^+$ calculated for $C_{43}H_{65}N_{11}O_{11}S_2$=976.4).

Example 4

Use of the Peptide C$^\alpha$-Amide of General Formula (II) in a Native Chemical Ligation (NCL) Reaction The use of a peptide C$^\alpha$-amide 14' of general formula (II) in a native chemical ligation reaction is illustrated in FIG. 23.

The peptide C$^\alpha$-amide of general formula (II) (compound 14'), by virtue of its crypto-thioester properties, can be used directly in an NCL native chemical ligation reaction, without converting it beforehand to the peptide C$^\alpha$-thioester (FIG. 23).

Preparation of the Cysteinyl Peptide 16 Partner

The peptide 16 (H—CRCIPVGLIGYCRNPSG-OH) was synthesized under standard conditions (ABI 433 synthesizer, Fastmoc program, coupling agent: HCTU). The resin obtained after automated elongation is treated for 2 h with 87.5:5:5:2.5 TFA/PhOH/H$_2$O/i-Pr$_3$SiH so as to detach and deprotect the peptide 16, which is precipitated by dilution in a 1:1 petroleum ether/Et$_2$O mixture, washed (Et$_2$O) and then dried. The precipitate is taken up in demineralized water and then lyophilized. It is then analyzed by HPLC and mass spectrometry (FIG. 24).

Peptide 16 (FIG. 24):
Molecular formula: $C_{81}H_{135}N_{25}O_{22}S_3$;
HPLC: $t_R$=24.3 min (gradient: 5-50% MeCN/H$_2$O+0.1% TFA over the course of 30 min);
UV detection ($\lambda$=276 nm);
MS (MALDI-TOF): m/z obtained=1906.9 ([MH]+ calculated for $C_{81}H_{136}N_{25}O_{22}S_3$=1906.9).

Native Chemical Ligation Between the Peptides 14'/14" and 16

2.5 μmol of crude crypto-thioester peptide 14'/14" and 1.5 equivalents of crude cysteinyl peptide 16 are dissolved in 1 ml of a deoxygenated solution containing 25 mM of mercaptophenylacetic acid, 50 mM of triscarboxyethylphosphine and 200 mM of phosphate buffer, pH=7. The reaction mixture is stirred for 3 h at 37° C. under an argon atmosphere. A peptide 17 and a compound 18 of general formula (Ia) are thus obtained. The peptide 17 is purified by semi-preparative HPLC and then lyophilized. It is obtained with a yield of 65%.

Peptide 17 (FIG. 25):
Molecular formula: $C_{156}H_{249}N_{45}O_{48}S_7$;
HPLC: $t_R$=14.6 min (gradient: 30-45% MeCN/H$_2$O+0.1% TFA over the course of 30 min);
UV detection ($\lambda$=276 nm);
MS (MALDI-TOF): m/z obtained=3745.6 ([M+H]$^+$ calculated for $C_{156}H_{250}N_{45}O_{48}S_7$=3745.6).

Native Chemical Ligation Between the Peptides 14'/14" and 16 Followed by a One-Pot Oxidative Folding 2.5 μmol of crude crypto-thioester peptide 14'/14" and 3.75 μmol (1.5 equivalents) of crude cysteinyl peptide 16 are dissolved in 1 ml of a deoxygenated solution containing 25 mM of mercaptophenylacetic acid, 50 mM of triscarboxyethylphosphine and 200 mM of phosphate buffer, pH=7. The reaction mixture is stirred for 3 h at 37° C. under an argon atmosphere. The reaction mixture is directly used in a step of oxidative folding of the ligation product 17 (final concentration of 17: 13 μM) by dilution in a 1:1 mixture of isopropanol and of a buffer containing 0.2 mM of Tris, pH 8.6, 2 mM of EDTA, 1.82 mM of glutathione (GSH) and 0.78 mM of oxidized glutathione (GSSG), and stirring of the resulting solution for 24 hours at 4° C. The mini-protein 19 comprising three disulfide bridges is purified by semi-preparative HPLC and then lyophilized. 19 is obtained with a yield of 55%.

Peptide 19 (FIG. 26):
Molecular formula: $C_{156}H_{243}N_{45}O_{48}S_7$;
HPLC: $t_R$=28.4 min (gradient: 30-45% MeCN/H$_2$O+0.1% TFA over the course of 30 min);
UV detection ($\lambda$=276 nm);
MS (MALDI-TOF): m/z obtained=3739.5 ([MH]+ calculated for $C_{156}H_{244}N_{45}O_{48}S_7$=3739.5).

The invention claimed is:

1. The peptide $C^\alpha$-amide having the general formula (II):

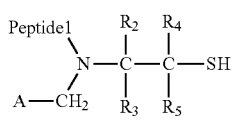
(II)

in which:

Peptide1 represents the $R_{18}$-$(Xaa)_k$- group in which:

k is an integer ranging from 1 to 100,

Xaa represents, independently of one another, an amino acid residue originating from an amino acid of formula H—Xaa-OH, and when k is greater than or equal to 2, each of said Xaa is connected to its neighboring Xaa via a peptide bond, $R_{18}$ is a hydrogen atom or a substituent of the N-terminal end included in the Xaa residue, one of $R_2$, $R_3$, $R_4$ or $R_5$ represents the radical —B—C-D in which:

D represents a hydrogen atom or a solid support suitable for solid phase peptide synthesis (SPPS), C is absent or represents an arm that can be used for SPPS, B represents:

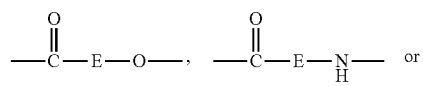

-continued

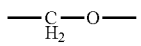

in which

E is absent or represents the -(Xaa)$_i$- group in which:

i represents an integer ranging from 1 to 20, each Xaa represents, independently of one another, an amino acid residue, and when i is greater than or equal to 2, each of said Xaa is connected to its neighboring Xaa via a peptide bond, the others of said $R_2$, $R_3$, $R_4$ or $R_5$ which do not represent —B—C—D, then represent, independently of one another, a hydrogen atom, or an alkyl radical having from 1 to 5 carbon atoms, or a phenyl radical (—$C_6H_5$), on the condition that at most two of said radicals $R_2$, $R_3$, $R_4$ or $R_5$ represent at the same time a phenyl, A represents an aryl or heteroaryl radical chosen from the group comprising the radical of formula:

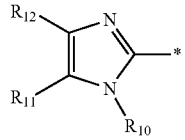

in which

* indicates the point of attachment of A in the compound of formula (II), $R_{10}$ represents an alkyl radical having from 1 to 10 carbon atoms, $R_{11}$ and $R_{12}$ represent, independently of one another, a hydrogen atom, a halogen atom chosen from the group comprising Cl, Br, I and F, a —CN radical, an —$NO_2$ radical, a —$CF_3$ radical, a phenyl radical (—$C_6H_5$), a —$CONH_2$ radical, an $R_{10}$ radical, an —$OR_{10}$ radical, an —$SR_{10}$ radical, an —$N(R_{10})_2$ radical, a —$COOR_{10}$ radical, a —$CONHR_{10}$ radical or a —$CON(R_{10})_2$ radical, $R_{10}$ being as previously defined, the radical of formula:

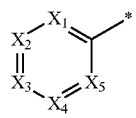

in which

* indicates the point of attachment of A in the compound of formula (II), at least one of $X_1$, $X_2$, $X_3$, $X_4$ and $X_5$ represents a nitrogen (N) atom, a C—OH radical or a C—SH radical, the others of said $X_1$, $X_2$, $X_3$, $X_4$ or $X_5$ which do not represent N, C—OH or C—SH, then representing, independently of one another, a C—$R_{11}$ radical with $R_{11}$ as previously defined, the radical of formula:

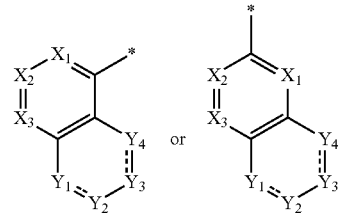

in which

* indicates the point of attachment of A in the compound of formula (II), at least one of $X_1$, $X_2$, $X_3$ and $Y_4$ represents a nitrogen (N) atom, a C—OH radical or a C—SH radical, the others of said $X_1$, $X_2$ or $X_3$ which do not represent N, C—OH or C—SH, then representing, independently of one another, a C—$R_{11}$ radical with $R_{11}$ as previously defined, $Y_1$, $Y_2$, $Y_3$ and $Y_4$ (on condition that $Y_4$ does not represent C—OH or C—SH) represent, independently of one another, depending on whether they are linked via a single or double bond, a nitrogen (N) atom or an $NR_{10}$ group with $R_{10}$ as previously defined, a CH or $CH_2$ group, a C—$R_{11}$ or $CHR_{11}$ or $CR_{11}R_{12}$ group with $R_{11}$ and $R_{12}$ as previously defined, a carbonyl (C=O), an oxygen (O) atom or a sulfur (S) atom, with the condition that at most two of said $Y_1$, $Y_2$, $Y_3$ and $Y_4$ represent at the same time an oxygen atom or a sulfur atom, one of said $Y_1$, $Y_2$, $Y_3$ or $Y_4$ possibly being absent, so as to form a 5-membered ring, thereby promoting an intramolecular rearrangement of said peptide $C^\alpha$-amide (II) leading to the following peptide thioester (II-1):

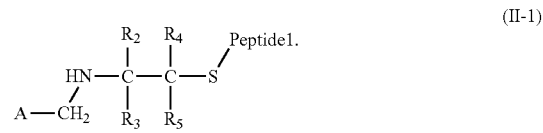

2. The peptide $C^\alpha$-amide as claimed in claim 1, wherein C represents an arm that can be used for Fmoc SPPS.

3. The peptide $C^\alpha$-amide as claimed in claim 2, wherein C represents an acid-labile arm chosen from the group comprising a Rink (4-[(2,4-dimethoxyphenyl)methyl]phenoxyacetyl) arm, a Wang (4-alkoxybenzyl) arm, a Sieber (xanthen-3-yloxyalkyl) arm, a PAL (4-2,5-dimethoxyalkoxybenzyl) arm, a 2-chlorotrityl arm, a PAM (phenylacetamidomethyl) arm, a SASRIN (2-methoxy-4-alkoxybenzyl) arm or an MBHA (4-methyl)benzhydryl arm.

4. The peptide $C^\alpha$-amide as claimed in claim 1, wherein D represents a solid support suitable for Fmoc SPPS and is chosen from the group comprising a polyacrylamide resin, a polystyrene resin or a polystyrene/polyethylene glycol (PEG) mixed resin.

5. The peptide $C^\alpha$-amide as claimed in claim 1, wherein the radical A has the formula:

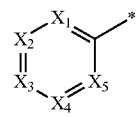

in which $X_1$ represents C—OH, and each of $X_2$, $X_3$, $X_4$ and $X_5$ is as defined in claim 1 and * indicates the point of attachment of A in the compound of formula (II).

6. The peptide $C^{60}$-amide as claimed in claim 5, wherein each of $X_2$, $X_3$ or $X_5$ represents CH and $X_4$ represents C—$R_{11}$ with $R_{11}$ as defined in claim 1.

7. The peptide $C^\alpha$-amide as claimed in claim 1, wherein n is an integer equal to 0, and the radical A has the formula:

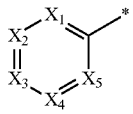

in which $X_1$ represents a nitrogen (N) atom and each of said $X_2$, $X_3$, $X_4$ and $X_5$ is as defined in claim 1.

8. The peptide $C^\alpha$-amide as claimed in claim 7, wherein each of $X_2$, $X_3$ or $X_5$ represents CH and $X_4$ represents CH or C—$R_{11}$ with $R_{11}$ representing $OCH_3$ or $N(CH_3)_2$.

9. The peptide $C^\alpha$-amide as claimed in claim 1, wherein n is an integer equal to 0, and the radical A has the formula:

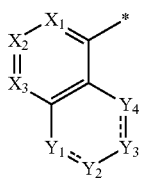

in which $X_1$ or $Y_4$ represents C—OH or N, the other said $X_1$ or $Y_4$ which does not represent C—OH or N, and also each of said $X_2$, $X_3$, $Y_1$, $Y_2$ and $Y_3$ are as defined in claim 1.

10. The peptide $C^\alpha$-amide as claimed in claim 1, wherein n is an integer equal to 0, and the radical A has the formula:

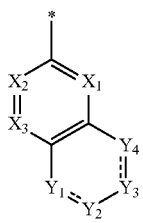

in which $X_1$ or $X_2$ represents C—OH or N, the other of said $X_1$ or $X_2$ which does not represent C—OH or N and also each of said $X_3$, $Y_1$, $Y_2$, $Y_3$ and $Y_4$ are as defined in claim 1.

11. The peptide $C^\alpha$-amide as claimed claim 1, wherein: each of said $R_3$, $R_4$, or $R_5$ represents H, $R_2$ represents —B—C-D in which B represents:

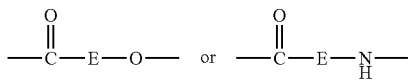

and C, D, and E are as defined in claim 1.

12. A process for preparing a peptide $C^\alpha$-amide of formula (II) as defined in claim 1 by Fmoc SPPS, comprising a step of elongation of the compound (Ia)

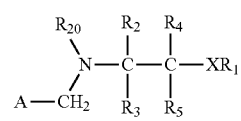

wherein
X represents a sulfur or selenium atom;
$R_1$ represents a hydrogen atom or a protective group for the sulfur or for the selenium which is compatible with conditions of elongation by Fmoc SPPS;
one of $R_2$, $R_3$, $R_4$ or $R_5$ represents the radical —B—C-D in which:
  D represents a hydrogen atom or a solid support suitable for SPPS,
  C is absent or represents an arm that can be used for SPPS,
  B represents a divalent radical comprising a heteroatom,
the others of said $R_2$, $R_3$, $R_4$ or $R_5$ which do not represent —B—C-D, then represent, independently of one another, a hydrogen atom, or an alkyl radical having from 1 to 5 carbon atoms, or a phenyl radical (—$C_6H_5$), on the condition that at most two of said radicals $R_2$, $R_3$, $R_4$ or $R_5$-represent at the same time a phenyl,
$R_{20}$ represents a hydrogen or $R_{14}$,
  $R_{14}$ represents $R_{13}$ and $R_{13}$ represents a protective group for the amine function, or
  $R_{14}$ represents a protected aminoacyl residue of formula $R_{13}$-Xaa-with Xaa representing an amino acid residue originating from an amino acid of formula H—Xaa-OH,
A represents an aryl or heteroaryl radical chosen from the radical of formula:

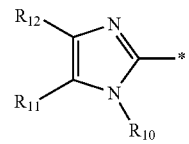

in which
* indicates the point of attachment of A in the compound of formula (Ia),
$R_{10}$ represents an alkyl radical having from 1 to 10 carbon atoms,
$R_{11}$ and $R_{12}$ represent, independently of one another, a hydrogen atom, a halogen atom chosen from Cl, Br, I and F, a —CN radical, an —$NO_2$ radical, a —$CF_3$ radical, a phenyl radical (—$C_6H_5$), a —$CONH_2$ radical, an $R_{10}$ radical, an —$OR_{10}$ radical, an —$SR_{10}$ radical, an —$N(R_{10})$ radical, a —$COOR_{10}$ radical, a —$CONHR_{10}$ radical or a —$CON(R_{10})_2$ radical, with $R_{10}$ as previously defined,
the radical of formula:

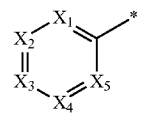

in which
* indicates the point of attachment of A in the compound of formula (Ia),
at least one of $X_1$, $X_2$, $X_3$, $X_4$ and $X_5$ represents a nitrogen (N) atom, a C—OH radical or a C—SH radical, the others of said $X_1$, $X_2$, $X_3$, $X_4$ or $X_5$ which do not represent N, C—OH or C—SH, then representing, independently of one another, a C—$R_{11}$ radical with $R_{11}$ as previously defined,
the radical of formula:

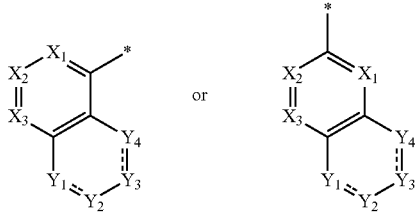

in which
* indicates the point of attachment of A in the compound of formula (Ia),
at least one of $X_1$, $X_2$, $X_3$ and $Y_4$ represents a nitrogen (N) atom, a C—OH Radical or a C—SH radical, the others of said $X_1$, $X_2$, and $X_3$ which do not represent N, C—OH or C—SH, then representing, independently of one another,
a C—$R_{11}$ radical with $R_{11}$ as previously defined,
$Y_1$, $Y_2$, $Y_3$ and $Y_4$ (on condition that $Y_4$ does not represent C—OH or C—SH) represent, independently of one another, depending on whether they are linked via a single or double bond, a nitrogen (N) atom or an $NR_{10}$ group with $R_{10}$ as previously defined, a CH or $CH_2$ group, a C—$R_{11}$ or $CHR_{11}$ or $CR_{11}R^{12}$ group with $R_{11}$ and $R_{12}$ as previously defined, a carbonyl (C=O), an oxygen (O) atom or a sulfur (S) atom, with the condition that at most two of said $Y_1$, $Y_2$, $Y_3$ and $Y_4$ represent at the same time an oxygen atom or a sulfur atom, one of said $Y_1$, $Y_2$, $Y_3$ or $Y_4$ possibly being absent, so as to form a 5-membered ring
said elongation step making it possible to add Peptide1 as defined in claim 1.

13. A process for preparing a peptide $C^\alpha$-thioester of general formula (IX):

Peptide1-S—R'  (IX)

in which:
R'— represents a radical originating from a thiol of formula R'—SH, and is an alkyl, aryl, arylalkyl, cycloalkyl, heterocycloalkyl or heteroaryl group, it being possible for each of said groups to also comprise one or more conventional substituents chosen from halogen, carboxyl, sulfonate, ammonium, alcohol, ether, alkyl, cycloalkyl, heterocycloalkyl, aryl, heteroaryl, alkoxy, haloalkyl, arylalkyl, heteroarylalkyl and arylheterocycloalkyl
Peptide1 is as defined in claim 1,
said process comprising a reaction for thioesterification between the peptide $C^\alpha$-amide of formula (II) as defined in claim 1, in which $R_1$ is equal to H, and a thiol of formula R'—SH,
in order to obtain the peptide $C^\alpha$-thioester of formula (IX) as defined above, and the compound of formula (Ib):

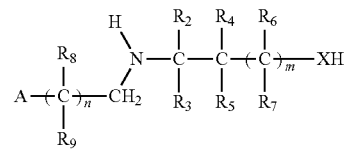

in which X, m, $R_2$, $R_3$, $R_4$, $R_5$, $R_6$, $R_7$, n, $R_8$, $R_9$ and A are as defined in claim 1.

14. A process for preparing a peptide of general formula (X):

Peptide1-Yaa-Peptide2-$R_{15}$  (X)

in which:
Peptide1 is as defined in claim 1,
Yaa is an amino acid residue originating from an amino acid of formula H—Yaa-OH chosen from the group comprising a cysteine, a homocysteine, a β-mercaptovaline, a β-mercaptoleucine, a β-mercaptoisoleucine, a β-mercaptophenylalanine, aβ-mercaptoproline, a β-mercaptoproline, a γ-mercaptovaline, a γ-mercaptoisoleucine, a γ-mercaptoleucine, a γ-mercaptolysine, a γ-mercaptoproline, or an amino acid substituted on its nitrogen atom $N^\alpha$ with a group containing a β- or γ-aminothiol function, said group being chosen from the group comprising:

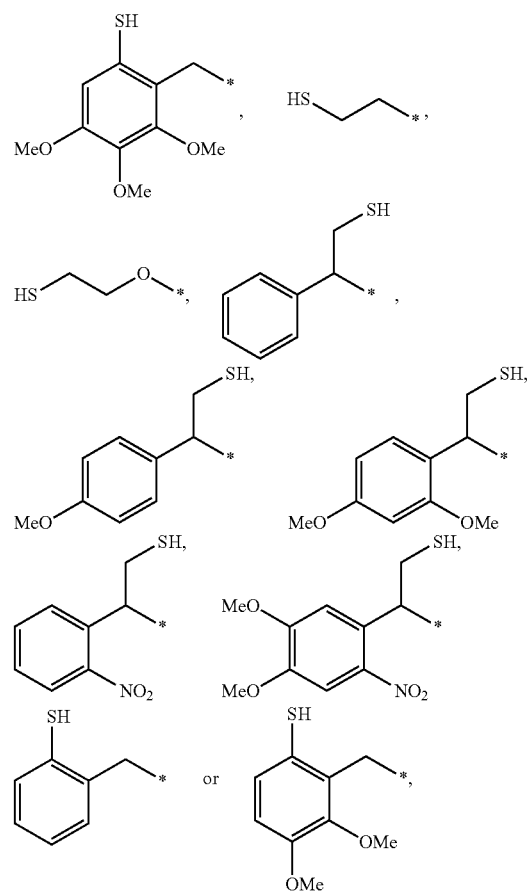

Peptide2=$(Xaa)_l$, with l=an integer ranging from 1 to 60,
Xaa represents, independently of one another, an amino acid residue originating from an amino acid of formula H—Xaa-OH, and when l is greater than or equal to 2, each of said Xaa is connected to its neighbor Xaa via a peptide bond, $R_{15}$ represents —OH, —$NH_2$ or a radical of general formula (I) in which X represents a sulfur atom and $R_1$ is a protective group for sulfur which is stable with respect to a treatment with TFA and stable under NCL conditions, wherein:

a peptide $C^\alpha$-amide of general formula (II) as defined in claim 1, in which $R_1$=H or a group which is labile under NCL native chemical ligation conditions, is reacted, by means of an NCL reaction, with a peptide possessing an N-terminal β- or γ-aminothiol residue of general formula (XI):

H—Yaa-Peptide2-$R_{15}$ (XI)

in which Yaa, $R_{15}$ and Peptide2 are as defined above,
in order to obtain
the peptide of general formula (X) as defined above and the compound of formula (Ia)

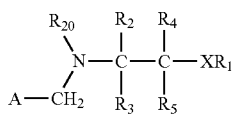

(Ia)

wherein

X represents a sulfur or selenium atom;

$R_1$ represents a hydrogen atom or a protective group for the sulfur or for the selenium which is compatible with conditions of elongation by Fmoc SPPS;

one of $R_2, R_3, R_4$ or $R_5$ represents the radical —B—C-D in which:

D represents a hydrogen atom or a solid support suitable for SPPS,

C is absent or represents an arm that can be used for SPPS,

B represents a divalent radical comprising a heteroatom, the others of said $R_2, R_3, R_4$ or $R_5$ which do not represent —B—C-D, then represent, independently of one another, a hydrogen atom, or an alkyl radical having from 1 to 5 carbon atoms or a phenyl radical (—$C_6H_5$), on the condition that at most two of said radicals $R_2, R_3, R_4$ or $R_5$-represent at the same time a phenyl, $R_{20}$ represents a hydrogen or $R_{14}$, $R_{14}$ represents $R_{13}$ and $R_{13}$ represents a protective group for the amine function, or $R_{14}$ represents a protected aminoacyl residue of formula $R_{13}$-Xaa-with Xaa representing an amino acid residue originating from an amino acid of formula H—Xaa-OH, A represents an aryl or heteroaryl radical chosen from the radical of formula:

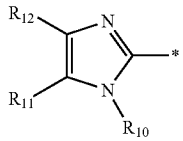

in which

* indicates the point of attachment of A in the compound of formula (Ia),3

$R_{10}$ represents an alkyl radical having from 1 to 10 carbon atoms, $R_{11}$ and $R_{12}$ represent, independently of one another, a hydrogen atom, a halogen atom chosen from Cl, Br, I and F, a —CN radical, an —$NO_2$ radical, a —$CF_3$ radical, a phenyl radical (—$C_6H_5$), a —$CONH_2$ radical, an $R_{10}$ radical, an —$OR_{10}$ radical, an —$SR_{10}$ radical, an —$N(R_{10})_2$ radical, a —$COOR_{10}$ radical, a —$CONHR_{10}$ radical or a —$CON(R_{10})_2$ radical, with $R_{10}$ as previously defined, the radical of formula:

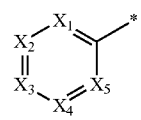

in which

* indicates the point of attachment of A in the compound of formula (Ia), at least one of $X_1, X_2, X_3, X_4$ and $X_5$ represents a nitrogen (N) atom, a C—OH radical or a C—SH radical, the others of said $X_1, X_2, X_3, X_4$ or $X_5$ which do not represent N, C—OH or C—SH, then representing, independently of one another, a C—$R_{11}$ radical with $R_{11}$ as previously defined, the radical of formula:

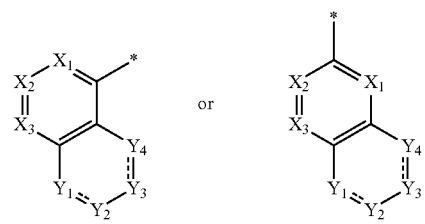

in which

* indicates the point of attachment of A in the compound of formula (Ia), at least one of $X_1, X_2, X_3$ and $Y_4$ represents a nitrogen N atom, a C—OH radical or a C—SH radical, the others of said $X_1, X_2$ and $X_3$ which do not represent N, C—OH or C—SH, then representing, independently of one another, a C—$R_{11}$ radical with $R_{11}$ as previously defined, $Y_1, Y_2, Y_3$ and $Y_4$ (on condition that $Y_4$ does not represent C—OH or C—SH) represent, independently of one another, depending on whether they are linked via a single or double bond, a nitrogen (N) atom or an $NR_{10}$ group with $R_{10}$ as previously defined, a CH or $CH_2$ group, a C—$R_{11}$ or $CHR_{11}$ or $CR_{11}R_{12}$ group with $R_{11}$ and $R_{12}$ as previously defined, a carbonyl (C=O), an oxygen (O) atom or a sulfur (S) atom, with the condition that at most two of said $Y_1, Y_2, Y_3$ and $Y_4$ represent at the same time an oxygen atom or a sulfur atom, one of said $Y_1, Y_2, Y_3$ or $Y_4$ possibly being absent, so as to form a 5-membered ring.

* * * * *